US012746265B2

(12) United States Patent
Coppee et al.

(10) Patent No.: US 12,746,265 B2
(45) Date of Patent: Sep. 29, 2026

(54) GINSENG COMPOSITION AND USE THEREOF AS A MEDICAMENT

(71) Applicant: BOTALYS SA, Ath (BE)

(72) Inventors: Paul-Evence Coppee, Ath (BE); Pierre-Antoine Mariage, Forest (BE); Sylvie Defrere, Isieres (BE)

(73) Assignee: BOTALYS SA, Ath (BE)

( * ) Notice: Subject to any disclaimer, the term of this patent is extended or adjusted under 35 U.S.C. 154(b) by 822 days.

(21) Appl. No.: 17/753,391

(22) PCT Filed: Sep. 3, 2020

(86) PCT No.: PCT/EP2020/074649

§ 371 (c)(1),
(2) Date: Mar. 1, 2022

(87) PCT Pub. No.: WO2021/043927

PCT Pub. Date: Mar. 11, 2021

(65) Prior Publication Data

US 2022/0288147 A1 Sep. 15, 2022

Related U.S. Application Data

(63) Continuation of application No. PCT/EP2019/073494, filed on Mar. 9, 2019.

(30) Foreign Application Priority Data

Sep. 3, 2019 (BE) .................................. 2019/5586
Nov. 21, 2019 (BE) .................................. 2019/5810

(51) Int. Cl.

| | |
|---|---|
| ***A61K 36/258*** | (2006.01) |
| ***A61K 8/9789*** | (2017.01) |
| ***A61P 25/28*** | (2006.01) |
| ***A61Q 19/00*** | (2006.01) |
| ***A61Q 19/02*** | (2006.01) |
| ***A61Q 19/08*** | (2006.01) |

(52) U.S. Cl.

CPC .......... *A61K 36/258* (2013.01); *A61K 8/9789* (2017.08); *A61P 25/28* (2018.01); *A61Q 19/007* (2013.01); *A61Q 19/02* (2013.01); *A61Q 19/08* (2013.01); *A61K 2236/333* (2013.01)

(58) Field of Classification Search

CPC ................ A61K 36/258; A61K 8/9789; A61K 2236/333; A61P 25/28; A61Q 19/007; A61Q 19/02; A61Q 19/08

See application file for complete search history.

(56) References Cited

U.S. PATENT DOCUMENTS

| | | | |
|---|---|---|---|
| 5,663,160 | A | 9/1997 | Meybeck |
| 2007/0065526 | A1 | 3/2007 | Gow |
| 2012/0165266 | A1 | 6/2012 | Nah |

FOREIGN PATENT DOCUMENTS

| | | | |
|---|---|---|---|
| EP | 1198995 | A1 | 4/2002 |
| EP | 3072517 | A | 9/2016 |
| FR | 2767057 | A1 | 2/1999 |
| JP | 2009537466 | A | 10/2009 |
| JP | 2016128427 | A | 7/2016 |
| WO | 2005120536 | A1 | 12/2005 |
| WO | 2013176512 | A1 | 11/2013 |
| WO | 2021/043927 | A1 | 3/2021 |

OTHER PUBLICATIONS

Rajabian et al. Therapeutic potential of Panax ginseng and its constituents, ginsenosides and gintonin, in neurological and neurodegenerative disorders: a patent review. Expert Opinion on Therapeutic Patents, 2019, 29(1):55-72 (published online Dec. 11, 2018). (Year: 2018).*

Hwang Ji Eun et al, "Comparative study on anti-oxidative and anti-inflammatory properties of hydroponic ginseng and soil-cultured ginseng", Aug. 30, 2018 (Aug. 30, 2018), vol. 28, No. 1, p. 215-224.

Lee Seon-Ho et al, "Changes in ginsenoside patterns of red ginseng extracts according to manufacturing and storage conditions", Jul. 12, 2017 (Jul. 12, 2017), vol. 26, No. 6, p. 1735-1741.

Yu-Jin Kim et al, "Biosynthesis and biotechnological production of ginsenosides", Biotechnology Advances., vol. 33, No. 6, Nov. 1, 2015 (Nov. 1, 2015), p. 717-735.

Ik-Hyun Cho, "Effects of Panax ginseng in Neurodegenerative Diseases", Journal of Ginseng Research, vol. 36, No. 4, Oct. 15, 2012 (Oct. 15, 2012), p. 342-353.

Pierre-Antoine Mariage et al, "Efficacy of Panax ginseng Meyer Herbal Preparation HRG80 in Preventing and Mitigating Stress-Induced Failure of Cognitive Functions in Healthy Subjects: A Pilot, Randomized, Double-Blind, Placebo-Controlled Crossover Trial", Pharmaceuticals, vol. 13, No. 4, Mar. 29, 2020 (Mar. 29, 2020), p. 57.

Cho, Ik-Hyun. "Effects of Panax Ginseng in Neurodegenerative Diseases." Journal of Ginseng Research, vol. 36, No. 4, Elsevier BV, Oct. 15, 2012, pp. 342-353.

(Continued)

*Primary Examiner* — Robert A Wax

*Assistant Examiner* — Olga V. Tcherkasskaya

(74) *Attorney, Agent, or Firm* — Vorys, Sater, Seymour and Pease, LLP; Iona N. Kaiser

(57) ABSTRACT

The invention pertains to the composition for use as a medical or therapeutic substance for improving cognitive performance and methods for preparation thereof. The composition comprises a rare ginsenoside, a ginsan and a gintonin. Methods include growing a *ginseng* in a hydroponic environment, harvesting its root, and cooking the harvested root after drying and/or grinding the harvested root. Preferably, the ratio of ginsan to gintonin ranges from about 1:100 to about 500:1. Preferably, the ratio of rare ginsenosides to ginsan and gintonin is from about 1:40 to about 250:1.

14 Claims, 5 Drawing Sheets

(56) References Cited

OTHER PUBLICATIONS

Ginseng HRG80 in Stress and Fatigue, ClinicalTrials.gov, Aug. 16, 2024 Daily Search, Jul. 5, 2019, <https://clinicaltrials.gov/study/NCT03947554>.

* cited by examiner

GINSENG COMPOSITION AND USE THEREOF AS A MEDICAMENT

FIELD OF THE INVENTION

The invention pertains to a composition comprising a rare ginsenoside, a ginsan and a gintonin, a kit thereof, use thereof as a medical or therapeutic substance and preparation thereof.

BACKGROUND

The chemical constituents of *ginseng* from *Panax* and other genuses can be categorized as saponins, polysaccharides, flavonoids and volatile oils. Most biological activity of *ginseng* has been attributed to saponin (i.e. ginsenoside) constituents and their metabolites.

The proposed clinical applications of *ginseng* constituents include, but are not limited to, anti-hyperglycemic, antioxidant, anti-inflammatory, immune stimulating and anti-apoptotic effects. The biological activity of said constituents is proposed as being adaptogenic. Adaptogens enhance survival by promoting adaptability to stress. In particular, adaptogens modify the stress-response in a non-specific way to maintain homeostasis. An adaptogen acts as a mild stress mimetic and can be considered as a stress preparer. By repeated administration of an adaptogenic substance, a certain stress resistance can be obtained.

The effectiveness of *ginseng* constituents has been studied thoroughly. Most results are non-significant or difficult to interpret. Shergis et al. (2012) reviewed 475 clinical studies. Significant results were identified for an improved glucose metabolism and a moderation of the immune system. Other domains of interest showed no significant results (see e.g. psychomotor performance, physical performance, circulatory metabolism, respiratory metabolism, erectile dysfunction, quality of life, antioxidant, cancer, menopausal symptoms and dry mouth).

One explanation for said flawed results is an inadequate bioavailability of the different *ginseng* constituents. In particular, bioavailability has been shown to be limited for orally administered doses. Absorption rates as low as 0.1% of an orally administered dose of Rg1 and as low as 1.9% of an orally administered dose of Rg2 have been observed (Herbs, Botanicals and Teas, CRC Press 1998 pg. 28 G. Mazza, B. D. Oomah). Limited recovery of ginsenosides from tissues, faeces, and urine is likely caused by an extensive pre-systemic metabolism of ginsenosides (Masami, Takino, Yoshio, 1991). Studies have shown that brain tissue levels achieved for most of the ginsenosides are very low. These levels are unlikely to reach the concentrations in the brain necessary to elicit therapeutic effects.

WO 2018 148 821 proposes a method for improving cognition in the brain of a subject. The method comprises the step of administering, to the subject, a composition comprising an active combination of at least one phospholipid and at least one substance. The substance can be a ginsenoside. WO '821 proposes complexing ginsenosides in a phospholipid matrix to increase oral bioavailability of subject ginsenosides compared to aqueous solutions. In this regard, the applicant notes that an improvement in bioavailability does not necessarily correlates with an improved therapeutic effect.

It is an objective of the present invention to provide new, highly active and easily obtainable compounds and compositions for improving cognitive performance in a subject, for treatment or prevention of stress in a subject, and for improving skin conditions in a subject. It is especially an object of the invention to provide compounds and compositions for use in a medical treatment, preferably a medical treatment for improving or preventing an impaired cognition in a subject. It is also especially an object of the invention to provide compounds and compositions for treatment or prevention of stress in a subject, whereby the cognitive performance of said subject is improved. It is also especially an object of the invention to provide compounds and compositions for use in a medical treatment, preferably a medical treatment for treatment and/or prevention of a skin and/or dermatological disease in a subject. It is also an object of the current invention to provide for a method for preparing such compositions and for administering such compositions to a subject.

SUMMARY OF THE INVENTION

The current invention provides in a solution for at least one of the above-mentioned problems by providing compositions comprising a rare ginsenoside, a ginsan and a gintonin, their use as medical and cognition improving substances and more specifically for use as a medicament for treatment of prevention of an impaired cognition in a subject, their use as medical or therapeutic substances in a stress prevention and/or relieve treatment and more specifically their use in a stress prevention and/or relieve treatment whereby the cognition of a subject is improved, their use as medical or therapeutic substances and more specifically their use as a medicament for treatment or prevention of a skin and/or dermatological disease.

In a first aspect, the invention relates to a composition comprising a rare ginsenoside, a ginsan and a gintonin wherein the ratio of ginsan to gintonin is at least 500:1 and at most 1:100 and wherein the ratio of rare ginsenosides to ginsan and gintonin is at least 250:1and at most 1:4. The inventors have surprisingly found that such compositions exhibit an improved cognitive performance in a subject in contrast to traditional *Panax ginseng*-based compositions.

In a second, third and fourth aspect, the invention relates to a composition according to the first aspect of the invention for use as a medicament. Preferably a medicament for use in treatment or prevention of an impaired cognition in a subject. Furthermore, the composition can be used in treatment or prevention of stress in a subject. Furthermore, such compositions exhibit improved skin conditions in a subject, especially in contrast to traditional *Panax ginseng*-based compositions.

In a fifth, sixth, and seventh aspect, the invention relates to a method for treatment or prevention of an impaired cognition in a subject, treatment or prevention of stress in a subject, and improving skin conditions in a subject. The method comprising the step of administering a composition according to a first aspect of the invention and/or a composition according to a second aspect of the invention.

In an eighth aspect, the invention relates to a method for preparation of a medicament preferably a medicament for treatment or prevention of an impaired cognition in a subject, the medicament comprising: a daily effective dose of rare ginsenoside of at least 1 mg and at most 100 mg; a daily effective dose of ginsan of at least 0.3 mg and at most 30 mg; and a daily effective dose of gintonin of at least 0.1 mg and at most 10 mg, the method comprising the steps of: growing a ginseng in a hydroponic environment; harvesting a root from said grown ginseng; and grinding said harvested root to obtain said medicament. The medicament comprising daily effective doses of rare ginsenoside, ginsan and gintonin. The method comprising the step of growing ginsent in hydroponic condisions.

A medicament according to the first and/or second aspect of the invention is prepared according to the fourth aspect of the invention.

In a ninth aspect, the invention relates to a kit of the invention comprising one or more aliquots of a composition, said composition comprising a rare ginsenoside, a ginsan and a gintonin.

DETAILED DESCRIPTION OF THE INVENTION

Figure 1:
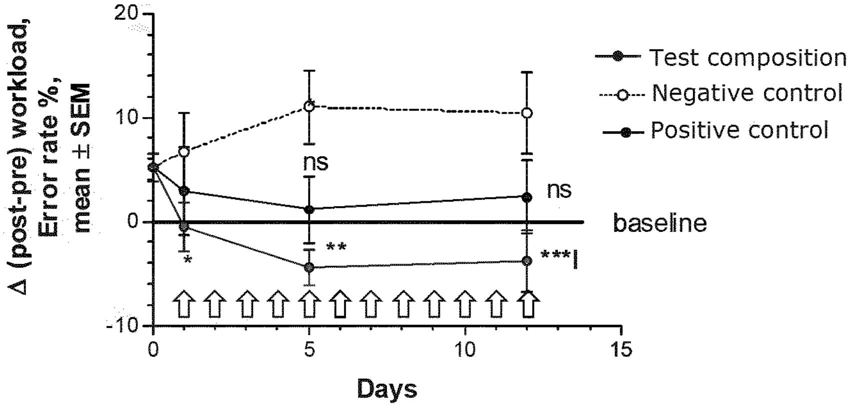
FIG. 1 shows the effect for the composition is obtained for a treatment over a period of days.

The invention pertains to a composition, use and preparation thereof for improving the cognitive performance in a subject, for treatment or prevention of stress in a subject, and for improving skin conditions in a subject. The invention also pertains to a kit according to the invention. The composition in essence comprising a rare ginsenoside, a ginsan and a gintonin. In what follows, the invention will be described in detail, preferred aspects and embodiments are discussed and the invention will be illustrated by means of non-limitative examples. The preferred aspects and embodiments as disclosed herein are nowhere intended to limit the scope of the present invention.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

“A”, “an”, and “the” as used herein refers to both singular and plural referents unless the context clearly dictates otherwise. By way of example, “a rare ginsenoside” refers to one or more than one rare ginsenoside, “a ginsan” refers to one or more than one ginsan and “a gintonin” refers to one or more than one gintonin.

“About” as used herein referring to a measurable value such as a parameter, an amount, a temporal duration, and the like, is meant to encompass variations of +/−20% or less, preferably +/−10% or less, more preferably +/−5% or less, even more preferably +/−% or less, and still more preferably +/−0.1% or less of and from the specified value, in so far such variations are appropriate to perform in the disclosed invention. However, it is to be understood that the value to which the modifier “about” refers is itself also specifically disclosed.

“Comprise”, “comprising”, and “comprises” and “comprised of” as used herein are synonymous with “include”, “including”, “includes” or “contain”, “containing”, “contains” and are inclusive or open-ended terms that specifies the presence of what follows e.g. component and do not exclude or preclude the presence of additional, non-recited components, features, element, members, steps, known in the art or disclosed therein.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The recitation of numerical ranges by endpoints includes all numbers and fractions subsumed within that range, as well as the recited endpoints. All percentages are to be understood as percentage by weight unless otherwise defined or unless a different meaning is obvious to the person skilled in the art from its use and in the context wherein it is used. The expression “% by weight”, “weight percent”, “% wt” or “wt %”, here and throughout the description unless otherwise defined, refers to the relative weight of the respective component based on the overall weight of the formulation.

Whereas the terms “one or more” or “at least one”, such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to “one embodiment” or “an embodiment” means that a particular feature, structure or characteristic described in connection with the embodiment is included in at least one embodiment of the present invention. Thus, appearances of the phrases “in one embodiment” or “in an embodiment” in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The current invention provides in a solution for at least one of the above-mentioned problems by providing a composition in essence comprising a rare ginsenoside, a ginsan and a gintonin.

1. Compositions of the Invention

In a first aspect, the invention relates to a composition for improving cognitive performance in a subject. Said composition preferably comprising a rare ginsenoside. Said composition preferably comprising a ginsan. Said composition preferably comprising a gintonin.

"Subject" as used herein, should be understood as a human or animal body. As used herein, "animal" preferably refers to vertebrates, more preferably to birds and mammals, and even more preferably to mammals. "Subject in need thereof" as used herein, should be understood as a patient, animal, or human, who will benefit from the treatment of this disclosure.

"Composition" as used herein, should be understood as comprising additional ingredients, additives, carriers, nutraceuticals, pharmaceutical compositions and physiologically acceptable compositions and so forth. It will be understood that where, for example, a rare ginsenoside, ginsan or gintonin in a "composition" also occurs in a natural source, the term "composition" does not include the natural source of the component, but can, in certain embodiments, encompass a physically or chemically modified or processed form of the natural source, such as an extract of the natural source.

"*Ginseng*" as used herein, should be understood as a species belonging to the genus *Panax* of the family Araliaceae. *Ginseng* may be available in various forms which are divided into fresh *ginseng*, white *ginseng*, and red *ginseng*, according to the processing method. Also, *ginseng* may be classified into artificially bred *ginseng*, artificially sown but wild-grown *ginseng*, and wild *ginseng* depending on the culturing conditions. In particular, the term "*ginseng*" as used herein is meant to include all kinds of *ginseng*, so that American *ginseng* and Chinese *ginseng* as well as Korean *ginseng* fall within the scope of the present disclosure.

"Ginsan" as used herein, should be understood as an acidic polysaccharide isolated from a species of the *Panax* genus. In particular, ginsan has a molecular weight of about 150 kDa and is composed of 3.7% proteins, 47.1% hexoses (glucose and galactose) and 43.1% uronic acid (galacturonic acid). Ginsan enhances the production of cytokines and reactive oxygen species (ROS) by macrophages (Shin et al., 2002) and stimulates the phagocytic activity of macrophages (Song et al., 2002). Since its initial purification, ginsan has been shown to have critical effects on immune cells (Lee et al., 1997). As an immunomodulator, ginsan plays a radioprotective role in hematopoietic and immune cells (Song et al., 2003). It increases the number of bone marrow (BM) cells, splenocytes, and some hematopoietic stem cells and enhances the production of cytokines involved in hematopoietic recovery (Kim et al., 2007). Therefore, ginsan appears to protect the host from ionizing radiation via its immunomodulatory activities.

"Gintonin" as used herein, should be understood as a glycolipoprotein fraction isolated from a species of the *Panax* genus. In particular, gintonin is a pentamer entity with a molecular weight of about 67 kDa and an apparent molecular weight of about 13 kDa. More in particular, gintonin has an amino acid composition comprising cysteine and cystine, asparagine and aspartic acid, glutamine and glutamic acid, serine, glycine, arginine, threonine, alanine, proline, valine, isoleucine, leucine, phenylalanine, tryptophan and lysine, a carbohydrate composition comprising rhamnose, arabinose, glucose, mannose, xylose and glucosamine, and a lipid composition comprising linoleic acid, palmitic acid, oleic acid and stearic acid. The protein composition of gintonin leads to an assumption that the carbohydrate portion of gintonin might be derived from N-glycosylations of *ginseng* major latex-like protein.

"Rare ginsenoside" as used herein, should be understood as synonym for the terms "prototype ginsenoside" or "noble ginsenosides" and refers to a class of tetracyclic triterpenoids and their derivates. Examples include, but are not limited to, Rg3, Rh1, C-K, Rh2, Rg5, Rk1, Rh3, Rk2, Rh4, Rk3, aPPT and aPPD. Preferably, the rare ginsenosides are selected from the group comprising: C-K, Rg6, Rh4, Rg3, PPT, Rk1, Rg5, Rh2, Rh3 and PPD.

The inventors have surprisingly found that compositions according to the invention exhibit an improved cognitive performance in a subject or a subject in need thereof in contrast to traditional *Panax ginseng*-based compositions. This is of special interest since such compounds are natural plant-based components. Such compounds are also easily obtainable, as will be illustrated below. Without being bound to any mechanistic theories, it is rationalized that such compositions exhibit said improved cognitive performance due to an improved adaptogenic effect.

"Improved" as used herein, should be understood as the ability of a compound, composition, agent, or method to improve a described symptom or condition based on the context in which the term "improve" is used. Preferably, improvement is by at least 10%, more preferably by at least 25%, even more preferably by at least 50%, and most preferably, the symptom or condition is improved by at least 75%.

"Reduced" as used herein, should be understood as the ability of a compound, composition, agent, or method to reduce or impede a described symptom or condition based on the context in which the term "reduce" is used. Preferably, reduction is by at least 10%, more preferably by at least 25%, even more preferably by at least 50%, and most preferably, the symptom or condition is reduced by at least 75%.

"Symptom" as used herein, should be understood as being interchangeable with the term "sign". Therefore, as used herein "symptom" refers to a physical and/or mental condition which indicates a particular illness or disorder (e.g. Longman Dictionary of Contemporary English (1995). Third edition) detectable by the subject suffering from a particular disease or disorder or detectable by a person other than the subject without verbal information from said subject.

Preferably in a composition according to a first aspect, the ratio of ginsan to gintonin is at least 500:1. The applicant notes that such ratio of ginsan to gintonin is at least required in order for the composition to elicit an improved cognitive performance and reduced stress level in a subject in contrast to traditional *Panax ginseng*-based compositions, more preferably the ratio of ginsan to gintonin is at least 490:1, even more preferably at least 490:1, even more preferably at least 450:1, preferably at least 400:1, even more preferably at least 350:1, even more preferably at least 300:1, even more preferably at least 250:1. The applicant notes that ratio of ginsan to gintonin of at least 200:1, elicits an even further improved cognitive performance and reduced stress level in a subject, more preferably the ratio of ginsan to gintonin is at least 250:1, even more preferably at least 200:1, even more preferably at least 150:1, even more preferably at least 100:1, even more preferably at least 150:1, even more preferably at least 100:1. The applicant notes that a ratio of ginsan to gintonin of at least 50:1 elicits an even more improved cognitive performance in a subject, more preferably the ratio of ginsan to gintonin is at least 45:1, even more preferably at least 40:1, even more preferably at least 35:1, even more preferably at least 30:1, even more preferably at least 25:1, even more preferably at least 20:1, even more preferably at least 17:1, even more preferably at least 15:1, even more preferably at least 12:1. The applicant notes that a ratio of ginsan to gintonin of at least 10:1 elicits an even further improved cognitive performance in a subject, more preferably the ratio of ginsan to gintonin is at least 9:1, even more preferably at least 8:1, even more preferably at least 7:1, even more preferably at least 6:1 and even more preferably at least 5:1.

Preferably in a composition according to a first aspect, the ratio of ginsan to gintonin is at most 1:100. The applicant notes that such ratio of ginsan to gintonin is at most required in such composition in order for the composition to elicit an improved cognitive performance and reduced stress level in a subject in contrast to traditional *Panax ginseng*-based compositions, more preferably the ratio of ginsan to gintonin is at most 1:90, even more preferably at most 1:80, even more preferably at most 1:70, even more preferably at most 1:60, even more preferably at most 1:50. The applicant notes that a ratio of ginsan to gintonin of at most 1:40 elicits a further improved cognitive performance and reduced stress level in a subject, more preferably at most 1:30, even more preferably at most 1:20, even more preferably at most 1:10. The applicant notes that a ratio of ginsan to gintonin of at most 1:5 elicits an even further improved cognitive performance and reduced stress level in a subject, more preferably at most 1:4, even more preferably at most 1:2, even more preferably at most 1:1, even more preferably at most 2:1 and even more preferably at most 3:1.

Most preferably, the ratio of ginsan to gintonin is about 1:4. The applicant notes the most improved cognitive performance in a subject at ratios of ginsan to gintonin of about 1:4. These observations are substantiated by examples 1-21.

Preferably in a composition according to a first aspect, the ratio of rare ginsenosides to ginsan and gintonin is at least 250:1. The applicant notes that such ratio of rare ginsenosides to a total amount of ginsan and gintonin is at least required in order for the composition to exhibit an improved cognitive performance and reduced stress level in a subject in contrast to traditional *Panax ginseng*-based compositions, more preferably the ratio of rare ginsenosides to ginsan and gintonin is at least 200:1, even more preferably at least 150:1, even more preferably at least 100:1. The applicant notes that a ratio of rare ginsenosides to a combination of ginsan and gintonin of at least 80:1 elicits a further improved cognitive performance and reduced stress level in a subject, more preferably the ratio of rare ginsenosides to ginsan and gintonin is at least 60:1, even more preferably at least 40:1, even more preferably at least 20:1, even more preferably at least 10:1. The applicant notes that a ratio of rare ginsenosides to a combination ginsan and gintonin of at least 8:1 elicits an even further improved cognitive performance in a subject, more preferably the ratio of rare ginsenosides to ginsan and gintonin is at least 6:1, even more preferably at least 4:1 and even more preferably at least 3:1.

Preferably in a composition according to a first aspect, the ratio of rare ginsenosides to ginsan and gintonin is at most 1:40. The applicant notes that such ratio of rare ginsenosides to a total amount of ginsan and gintonin is at most required in order for the composition to exhibit an improved cognitive performance and reduced stress level in a subject in contrast to traditional *Panax ginseng*-based compositions, more preferably the ratio of rare ginsenosides to ginsan and gintonin is at most 1:30, even more preferably at most 1:20, even more preferably at most 1:10. The applicant notes that a ratio of rare ginsenosides to a combination of ginsan and gintonin of at most 1:5 elicits a further improved cognitive performance in a subject, more preferably at most 1:4, even more preferably at most 1:3, even more preferably at most 1:2. The applicant notes that a ratio of rare ginsenosides to ginsan and gintonin of at most 1:1 elicits an even further improved cognitive performance and reduced stress level in a subject.

Most preferably, the ratio of rare ginsenosides to ginsan and gintonin is about 2:1. The applicant notes the most improved cognitive performance in a subject at ratios of rare ginsenosides to ginsan and gintonin of about 1:4. These observations are substantiated by examples 1-21.

In a preferred embodiment, the present invention provides a composition comprising a ratio of rare ginsenoside to ginsan of at least 300:1. The applicant notes that such ratio is at least required to obtain an improved cognitive performance and reduced stress level over the traditional *Panax ginseng*-based compositions, more preferably the composition comprises a ratio of rare ginsenoside to ginsan of at least 300:1 and at most 1:30, even more preferably at least 250:1 and at most 1:20, even more preferably at least 200:1 and at most 1:15, even more preferably at least 150:1 and at most 1:10, even more preferably at least 100:1 and at most 1:7. The applicant notes that a ratio of rare ginsenosides to ginsan of at least 50:1 and at most 1:5 elicits a further improved cognitive performance and reduced stress level in a subject, more preferably at least 40:1 and at most 1:4, even more preferably at least 30:1 and at most 1:3, preferably at least 20:1 and at most 1:2 and even more preferably at least 10:1 and at most 1:1. The applicant notes that a ratio of rare ginsenosides to ginsan of at least 5:1 and at most 1:1 elicits an even further improved cognitive performance and reduced stress level in a subject.

Most preferably, the ratio of rare ginsenosides to ginsan is about 2.5:1. The applicant notes the most improved cognitive performance in a subject at such ratios of rare ginsenosides to ginsan. These observations are substantiated by examples 1-21.

In a preferred embodiment, the present invention provides a composition comprising a ratio of rare ginsenoside to gintonin of at least 1000:1. The applicant notes that such ratio is at least required to obtain an improved effect over the traditional *Panax ginseng*-based compositions, more preferably the composition comprises a ratio of rare ginsenoside to ginsan of at least 1000:1 and at most 1:10, even more preferably at least 900:1 and at most 1:9, even more preferably at least 80:1 and at most 1:8, even more preferably at least 700:1 and at most 1:7, even more preferably at least 600:1 and at most 1:6, even more preferably at least 500:1 and at most 1:5, even more preferably at least 400:1 and at most 1:4, even more preferably at least 300:1 and at most 1:3, even more preferably at least 200:1 and at most 1:2. The applicant notes that a ratio of rare ginsenosides to gintonin of at least 100:1 and at most 1:1 elicits a further improved cognitive performance in a subject, more preferably at least 90:1 and at most 1:1, even more preferably at least 80:1 and at most 1:1, even more preferably at least 70:1 and at most 1:1, even more preferably at least 60:1 and at most 1:1. The applicant notes that a ratio of rare ginsenosides to gintonin of at least 50:1 and at most 1:1 elicits an even further improved cognitive performance in a subject, more preferably at least 40:1 and at most 1:1, even more preferably at least 30:1 and at most 1:1 and even more preferably at least 20:1 and at most 5:1.

Most preferably, the ratio of rare ginsenosides to gintonin is about 10:1. The applicant notes the most improved cognitive performance in a subject at such ratios of rare ginsenosides to ginsan. These observations are substantiated by examples 1-21.

In a preferred embodiment, the present invention provides a composition comprising one or more rare ginsenosides selected from the group: Rg6, Rh4, Rg3, PPT, Rk1, Rg5, Rh2, Rh3 and PPD. Preferably, at least 40 wt % of rare ginsenosides in said group is attributed to one or more ginsenosides selected from the group comprising: Rg6, Rh4, Rg3, Rk1 and Rg5, more preferably at least 45 wt %, more preferably at least 50 wt %, more preferably at least 55 wt %, more preferably at least 60 wt %, more preferably at least 65 wt % and most preferably at least 70 wt %.

In a preferred embodiment, the present invention provides a composition further comprising a ginsenoside.

"Ginsenoside" as used herein, should be understood as synonym for the term "panaxoside" and refers to a class of natural product steroid glycosides and triterpene saponins found in *ginseng*. It should be clear, that upon referring to "ginsenoside" herein, "rare ginsenosides" are excluded unless otherwise specified. Thus, upon referring to "ginsenoside" herein, reference is made to "classical ginsenosides" unless otherwise specified. In particular, ginsenosides have a basic structure composed of a gonane steroid nucleus having 17 carbon atoms arranged in a tetracyclic configuration. Ginsenoside compounds, including protopanaxadiol type of ginsenosides such as ginsenosides Rb1, Rb2, Rc and Rd, are known to those of skill in the art (see, e.g., Yu et al., Chem. Pharm. Bull. 2007, 55(2), 231-235; Court, "The Principal Active Chemicals in *Panax* species" in *Ginseng*: The Genus *Panax* (Court, ed., Harwood Academic Publishers, Amsterdam, The Netherlands, 2000). Preferably, the ginsenoside is selected from the group comprising: Rg1, Re, Rf, Rh1, Rg2, Rb1, Rc, Rb2 and Rd. More preferably, the ginsenoside is selected from the group comprising: Rg2, Rb1, Rc, Rb2 and Rd.

In a preferred embodiment, the present invention provides a composition comprising one or more ginsenosides selected from the group: Rg1, Re, Rf, Rh1, Rg2, Rb1, Rc, Rb2 and Rd. Preferably, at least 40 wt % of ginsenosides in said group is attributed to one or more ginsenosides selected from the group comprising: Rg2, Rb1, Rc, Rb2 and Rd, more preferably at least 45 wt %, more preferably at least 50 wt %, more preferably at least 55 wt %, more preferably at least 60 wt %, more preferably at least 65 wt % and most preferably at least 70 wt %.

In a preferred embodiment, the present invention provides a composition comprising a ratio of rare ginsenoside to ginsenoside of at least 200:1, more preferably at least 200:1 and at most 1:5, even more preferably at least 150:1 and at most 1:5, even more preferably at least 100:1 and at most 1:5, even more preferably at least 50:1 and at most 1:5, even more preferably at least 40:1 and at most 1:4, even more preferably at least 30:1 and at most 1:3, even more preferably at least 20:1 and at most 1:2, even more preferably at least 10:1 and at most 1:1 and most preferably at least 6:1 and at most 2:1 and most preferably of about 4:1.

In a preferred embodiment, the present invention provides a composition comprising Rg5 and Rh2 and optionally one or more rare ginsenosides selected from the group comprising: C-K, Rg6, Rh4, Rg3, PPT, Rk1, Rh3 and PPD. Preferably, the the ratio of a Rg5 and Rh2 to a total amount of rare ginsenoside is at least 1:1, more preferably at least 1:1 and at most 1:4. The applicant notes a higher efficacy for such ratios. More preferably, the ratio of a Rg5 and Rh2 to a total amount of rare ginsenoside is at least 1:1.5 and at most 1:2.5. More preferably, the ratio of a Rg5 and Rh2 to a total amount of rare ginsenoside is about 1:2. The applicant notes the highest efficacy at ratios of about 1:2.

In a preferred embodiment, the present invention provides a composition comprising a ginsenoside selected from the group comprising: Rg1, Re, Rf, Rh1, Rg2, Rb1, Rc, Rb2 and Rd and wherein the ratio of Rc to a total amount of rare ginsenoside and ginsenoside is at least 1:1, more preferably at least 1:1 and at most 1:3. The applicant notes a higher efficacy for such ratios. More preferably, the ratio of Rc to a total amount of rare ginsenoside and ginsenoside is at least 1:1.5 and at most 2.5. Most preferably, the ratio of Rc to a total amount of rare ginsenoside and ginsenoside is about 1:2. The applicant notes the highest efficacy at ratios of about 1:2.

In a preferred embodiment, the present invention provides a composition comprising a ginsenoside, whereby the ratio of one or more compounds selected from the group comprising: C-K, Rk1, Rh2, Rh3, Rh4, Rg2, Rg3 and Rg6 to a total amount of rare ginsenosides and ginsenosides in the composition is at least 1:4. The compounds from the group: C-K, Rk1, Rh2, Rh3, Rh4, Rg2, Rg3 and Rg6 have a high bioavailability compared to other rare ginsenosides or ginsenosides. Moreover, the applicant notes that the efficacy of the composition drastically increases at a ratio of at least 1:4. More preferably, the ratio of one or more compounds selected from the group comprising: C-K, Rk1, Rh2, Rh3, Rh4, Rg2, Rg3 and Rg6 to a total amount of rare ginsenosides and ginsenosides in the composition is at least 1:4 and at most 1:1, even more preferably at least 1:3 and at most 1:1.5 and most preferably about 1:2. The applicant notes the highest efficacy of the composition at ratios of about 1:2.

According to an embodiment, the present invention may provide a composition comprising a phospholipid. Phospholipids are lipids containing phosphoric acid residue in general, including soybean lecithin, egg yolk lecithin, phosphatidyl choline, phosphatidyl choline, phosphatidyl ethanolamine, and phosphatidyl serine, which are widely present in the nature, including in animals and plants. Phospholipids are found in the cells of the brain and nervous system of mammals and are commonly used in pharmaceutical preparations. Phospholipid molecules have a hydrophilic head and two hydrophobic long chains and have been used as pharmaceutical excipients. Complexing *ginseng* constituents in a phospholipid matrix has been shown to increase oral bioavailability of individual ginsenosides compared to aqueous solutions in animal models. Preferably, the phospholipid is formulated as a nanoparticle.

Additional Ingredient

The composition as disclosed herein may comprise an additional ingredient.

"Additional ingredient" as used herein, should be understood as including one or more of the following: excipients; surface active agents; dispersing agents; inert diluents; granulating and disintegrating agents; binding agents; lubricating agents; sweetening agents; flavouring agents; colouring agents; preservatives; physiologically degradable compositions such as gelatine; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions are known in the art and described, for example in Genaro, ed. (1985, Remington's Pharmaceutical Sciences, Mack Publishing Co., Easton, Pa.).

"Pharmaceutical composition" as used herein, should be understood as a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

Suitable excipients include carbohydrate or protein fillers such as sugars, including lactose, sucrose, mannitol, or sorbitol; starch from corn, wheat, rice, potato, etc.; celluloses such as methyl cellulose, hydroxypropylmethyl-cellulose, or sodium carboxymethylcellulose; and gums including Arabic and tragacanth; and proteins such as gelatine and collagen. Suitable disintegrating or solubilizing agents include agar, alginic acid or a salt thereof such as sodium alginate.

Other components such as preservatives, antioxidants, surfactants, absorption enhancers, viscosity enhancers or film forming polymers, bulking agents, diluents, colouring agents, flavouring agents, pH modifiers, sweeteners or taste-masking agents may also be incorporated into the composition. Suitable colouring agents include red, black, and yellow iron oxides and FD&C dyes such as FD&C Blue No. 2 and FD&C Red No. 40. Suitable flavouring agents include mint, raspberry, liquorice, orange, lemon, grapefruit, caramel, vanilla, cherry grape flavours and combinations thereof. Suitable pH modifiers include citric acid, tartaric acid, phosphoric acid, hydrochloric acid, maleic acid and sodium hydroxide. Suitable sweeteners include aspartame, acesulfame K and thaumatin. Suitable taste-masking agents include sodium bicarbonate, vanilla, ion-exchange resins, cyclodextrin inclusion compounds and adsorbates.

Carrier

The composition as disclosed herein may comprise a carrier.

The composition as disclosed herein may comprise a nutritionally acceptable carrier. The composition as disclosed herein may comprise a pharmaceutically acceptable carrier. The composition as disclosed herein may comprise a cosmetically acceptable carrier.

"Nutritionally acceptable carrier" as used herein, should be understood as any nutritional supplement, nutritional product, food product and/or dietary item with which the composition and in particular the essential constituents of the composition (rare ginsenoside, ginsan and gintonin) can be combined and which, following the combination, can be used orally to administer the composition to a subject. Nutritionally acceptable carriers are known to the person skilled in the art.

Examples of nutritional acceptable carriers are flour, bread dough, breakfast cereals, snack bars, ready-to-eat meals and drinks (e.g., soft drink, soy milk, etc.). Upon combining the composition and in particular the essential constituents of the composition in a nutritional acceptable carrier, a nutritionally enhanced food item is formed that can then be further processed or packaged.

"Pharmaceutically acceptable carrier" as used herein, should be understood as a chemical composition with which the composition and in particular the essential constituents of the composition (rare ginsenoside, ginsan and gintonin) can be combined and which, following the combination, can be used orally to administer the composition to a subject. Pharmaceutically acceptable carriers are known to the person skilled in the art.

Examples of pharmaceutically acceptable carriers are sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Examples of suitable pharmaceutical carriers are described in Remington: Science and Practice of Pharmacy, 21st ed., Lippincott Williams & Wilkins, Philadelphia Pa. (2005) and Ansel's Pharmaceutical Dosage Forms and Drug Delivery Systems, 8th ed., Lippincott Williams & Wilkins, Philadelphia Pa. (2004).

"Cosmetically acceptable carrier" as used herein, should be understood as a chemical composition with which an appropriate compound or derivative can be combined and which, following the combination, can be used topically to administer the composition to a subject. Cosmetically acceptable carriers are known to the person skilled in the art.

"Topical application" as used herein, should be understood as an administration to a surface, such as the skin. This term is used interchangeably with "cutaneous application" in the case of skin. A "topical application" is a "direct application". "Suitable carrier" as used herein, should be understood as a cosmetically acceptable liquid medium, and preferably to a pharmaceutically acceptable liquid medium as commonly used in gels, lotions, shampoos, liquid soaps, etc. The skilled person will readily distinguish a "cosmetically acceptable liquid medium" and "a pharmaceutically acceptable liquid medium" from "cosmetically non-acceptable liquid medium" and "a pharmaceutically non-acceptable liquid medium" respectively.

Additive

The composition as disclosed herein may comprise an additive.

In addition to the essential components described hereinbefore, the present compositions may further comprise one or more optional components that are known or otherwise suitable for use on human/animal hair or skin.

Non-limiting examples of such optional components include for instance a foaming agent, plasticizers and humectants (such as glycerol, propane-1,2-diol, polypropylene glycol and other polyhydric alcohols), free radical scavengers, viscosity-adjusting agents, dyes and colorants, perfumes, preservatives and the like. In a preferred embodiment, the present composition further comprises a foaming agent. Foaming agents are agents, which promote the formation of the foam. Any agent having a surfactant character may be used. The surfactants may be cationic, non-ionic or anionic. Examples of suitable foaming agents include, but are not limited to cetrimide, lecithin, soaps, and the like, and for instance, anionic (based on sulfate, sulfonate or carboxylate anions): sodium dodecyl sulfate (SDS), ammonium lauryl sulfate, and other alkyl sulfate salts, Sodium laureth sulfate, also known as sodium lauryl ether sulfate (SLES), alkyl benzene sulfonate; soaps or fatty acid salts (see acid salts); cationic (based on quaternary ammonium cations): cetyl trimethylammonium bromide (CTAB) a.k.a. hexadecyl trimethyl ammonium bromide, and other alkyltrimethylammonium salts, cetylpyridinium chloride (CPC), polyethoxylated tallow amine (POEA), benzalkonium chloride (BAC), benzethonium chloride (BZT); zwitterionic (amphoteric): dodecyl betaine, dodecyl dimethylamine oxide, cocamidopropyl betaine, coco ampho glycinate; nonionic: alkyl poly(ethylene oxide), alkyl polyglucosides, including: octyl glucoside, decyl maltoside, fatty alcohols, cetyl alcohol, oleyl alcohol. Commercially available surfactants such as TWEEN™ are also suitable.

In a preferred embodiment, the compositions according to the invention are stored at room temperature, and preferably at a temperature below room temperature, such as at a temperature below 20° C., below 15° C., below 10° C. or below 5° C. Preferably, said compositions are stored at a temperature of about 4° C. For reasons of effective handling, it is preferred that the compositions are stored at a temperature above the melting temperature of the carrier.

Kit of the Composition

In a sixth aspect, the invention relates to a kit comprising one or more aliquots of a composition comprising a rare ginsenoside, a ginsan and a gintonin. Preferably, the composition is a composition according to a first and/or second aspect of the invention.

The kit may comprise an aliquot for each separate constituent of the composition disclosed herein. The kit may also comprise an aliquot for any combination of separate constituents of the composition disclosed herein.

Optionally the kit comprises an instructional material.

"Instructional material" as used herein, should be understood as including a publication, a recording, a diagram, or any other medium of expression which can be used to communicate the usefulness of a compound of the disclosure in the kit for effecting alleviation of the various diseases or disorders recited herein. Optionally, or alternately, the instructional material may describe one or more methods of alleviating the diseases or disorders in a subject. The instructional material of the kit may, for example, be affixed to a container which contains the identified compound disclosure or be shipped together with a container which contains the identified compound. Alternatively, the instructional material may be shipped separately from the container with the intention that the instructional material and the compound be used cooperatively by the recipient.

2. Use of a Composition of the Invention

Impaired Cognition

In a second aspect, the invention relates to a composition for use as a medicament. Preferably a medicament for treatment or prevention of an impaired cognition in a subject. Preferably, for said purpose, the composition is provided in a pharmaceutically or cosmetically acceptable carrier. Preferably, for said purpose, the composition is provided in one or more pharmaceutically acceptable excipients.

In a fifth aspect, the invention relates to a method for improving cognitive performance in a subject. Preferably, the method for treatment or prevention of an impaired cognition in a subject. The method comprising the step of administering, to the subject, a composition according to a first aspect and/or a composition according to a second aspect.

In accordance with the present invention, a composition comprising a rare ginsenoside, a ginsan and a gintonin as disclosed herein is used for improving cognitive performance in a subject. Said composition may also be used for treatment of an impaired cognition in a subject in need thereof. Use of the present composition includes prophylactic use.

"Treating" as used herein, should be understood as including prophylaxis of the specific injury, disease, disorder, or condition, or alleviation of the symptoms associated with a specific injury, disease, disorder, or condition and/or preventing or eliminating said symptoms. "Treating" is used interchangeably with "treatment" herein.

"Prevent" as used herein, should be understood as a means to stop something from happening, or taking advance measures against something possible or probable from happening. In the context of medicine, "prevention" generally refers to action taken to decrease the chance of getting a disease or condition.

"Prophylactic" treatment as used herein, should be understood as a treatment administered to a subject who does not exhibit signs of a disease or injury or exhibits only early signs of the disease or injury for the purpose of decreasing the risk of developing pathology associated with the disease or injury.

Effects of cognitive impairment include, but are not limited to, memory loss, learning difficulties and concentration or attention difficulties. Cognitive impairment in a subject might be caused by a wide array of different conditions. Examples include, but are not limited to, stress, fatigue, aging and a variety of conditions or disorders. Examples of such conditions and disorders include, but are not limited to, Lewy body dementia, vascular dementia, Alzheimer's Disease, HIV associated dementia, Huntington's Disease, Parkinson's Disease, amyotrophic lateral sclerosis, MCI and ARCD. Individuals with such conditions or disorders might have cognitive symptoms that increase in severity over the course of the disease.

In an alternative embodiment, the invention relates to a composition for use as a medicament for treatment or prevention of stress in a subject. Preferably, a medicament for treatment or prevention of stress in a subject whereby the cognitive performance of said subject is improved. Upon treating a subject for symptoms associated with stress, the cognition of said subject is likely improved.

In an alternative embodiment, the invention relates to a composition for use as a medicament for improving skin conditions in a subject. In an alternative embodiment, the invention relates to a composition for treatment and/or prevention of a skin and/or dermatological disease, preferably said skin and/or dermatological disease being related to an inflammation, an allergic reaction, a contact hypersensitivity reaction or intolerance, an excessive sebaceous secretion, an exfoliation or a microbial dysbiosis, preferably of the epidermis.

"Disorder" as used herein, should be understood as a subject in a state of health, in which the subject is able to maintain homeostasis, but in which the subject's state of health is less favorable than it would be in the absence of the disorder. Left untreated, a disorder does not necessarily cause a further decrease in the subject's state of health. In the context of the present application, stress may be considered as being a disorder. In the context of the present application, a reduced skin condition may be considered as being a disorder.

Without being bound to any mechanistic theories, it is rationalized that the compositions exhibit said cognition improving performance due to an improved adaptogenic effect. Without being bound to any mechanistic theories, it is rationalized that the compositions exhibit said medical or therapeutic effect in improving an impaired cognition in a subject due to an improved adaptogenic effect.

"Adaptogen" as used herein should be understood as an agent which raises a subject's nonspecific resistance to various physical, chemical or biological stressors (see adaptogenic effect). Adaptogens generally accomplish this by either regulating the activity of hyperfunctioning systems. Examples of adaptogens include, but are not limited to, *Astragalus* root, *Cordyceps*, Maca root, Schisandra berry, Ashwagandha root, Holy basil leaf, Reishi mushroom, Maitake mushroom, Suma root. Other adaptogens which are both non-toxic to the subject and are capable of raising the subject's nonspecific resistance to external stressors are also included as example.

The method for treatment or prevention of an impaired cognition in a subject comprises at least the step of administering the composition to a subject. The composition may be administered to a subject in an effective amount according to any method known in the art. Preferably, the composition is formulated for oral administration. The composition may be administered to a subject in the form of a tablet, a lozenge, a pill, a capsule, a hard gelatine capsule, etc. Preferably, the composition is enclosed in a capsule suitable for oral administration to a subject. A daily effective dose of the composition may be administered in 1, 2, 3, 4, 5, 6, 7, 8, 9, 10, 11, 12, 13, 14, 15, 16, 17, 18, 19 and 20 different doses. Preferably, a daily effective dose is at most administered in five different doses. More preferably, a daily effective dose is administered in two different doses. Preferably, one of said two different doses is administered after breakfast. Preferably, one of said two different doses is administered after dinner. More preferably, a daily effective dose is administered in one dose. Said one dose preferably being administered after breakfast.

A daily effective dose of ginsenoside and rare ginsenoside in the composition is preferably at least 1 mg, more preferably at least 1 mg and at most 150 mg, even more preferably at least 10 mg and at most 100 mg, even more preferably at least 15 mg and at most 75 mg, even more preferably at least 20 mg and at most 55 mg, even more preferably at least 30 mg and at most 45 mg and most preferably about 37.5 mg.

A daily effective dose of rare ginsenoside in the composition is preferably at least 1 mg, more preferably at least 1 mg and at most 100 mg, even more preferably at least 10 mg and at most 80 mg, even more preferably at least 15 mg and at most 70 mg, even more preferably at least 20 mg and at most 60 mg, even more preferably at least 25 mg and at most 50 mg and most preferably about 30 mg.

A daily effective dose of ginsenoside in the composition is preferably at least 1 mg, more preferably at least 1 mg and at most 100 mg, even more preferably at least 2.5 mg and at most 75 mg, even more preferably at least 5 mg and at most 50 mg, even more preferably at least 5 mg and at most 30 mg, even more preferably at least 6 mg and at most 15 mg and most preferably about 7.5 mg.

A daily effective dose of ginsan and gintonin in the composition is preferably at least 1 mg, more preferably at least 1 mg and at most 35 mg, even more preferably at least 2 mg and at most 33 mg, even more preferably at least 4 mg and at most 31 mg, even more preferably at least 6 mg and at most 29 mg, even more preferably at least 8 mg and at most 24 mg and most preferably about 16 mg.

A daily effective dose of ginsan in the composition is preferably at least 0.3 mg, more preferably at least 0.3 mg and at most 30 mg, even more preferably at least 1 mg and at most 27 mg, even more preferably at least 5 mg and at most 25 mg, even more preferably at least 7 mg and at most 20 mg, even more preferably at least 10 mg and at most 17 mg and most preferably about 13 mg.

A daily effective dose of gintonin in the composition is preferably at least 0.1 mg, more preferably at least 0.1 mg and at most 10 mg, even more preferably at least 0.3 mg and at most 8 mg, even more preferably at least 0.5 mg and at most 7 mg, even more preferably at least 0.7 mg and at most 6 mg, even more preferably at least 1 mg and at most 5 mg and most preferably about 3 mg.

In an especially preferred embodiment, the composition comprises a combination of a rare ginsenoside, ginsan and gintonin at respective daily effective doses of about 32 mg rare ginsenoside, at least 10 and at most 16 mg ginsan and at least 1 mg and at most 5 mg gintonin. Preferably, at respective daily effective doses of about 32 mg rare ginsenoside, 13 mg ginsan and at least 1 mg and at most 5 mg gintonin. Preferably, at respective daily effective doses of about 32 mg rare ginsenoside, at least 10 and at most 16 mg ginsan and 3 mg gintonin. Most especially preferred, at respective daily effective doses of about 32 mg rare ginsenoside, 13 mg ginsan and 3 mg gintonin. The applicant notes the most more improved cognitive performance in a subject at such daily effective doses. This is for example substantiated in examples 1-21.

Preferably, the composition further also comprises a combination of compounds comprising a rare ginsenoside, ginsan and gintonin at a ratio of ginsan to rare ginsenoside of about 4:1 and a ratio of ginsan to gintonin of about 2:1, more preferably said composition further comprising a ratio of rare ginsenoside to ginsan of about 2.5:1, even more preferably said composition further comprising a ratio of rare ginsenoside to gintonin of about 10:1. As is exemplified in examples 1-21, the applicant notes the most improved cognitive performance in a subject at such ratios, especially when said ratios are provided at preferred daily effective doses as disclosed hereabove.

In an especially preferred embodiment, the present invention provides a composition comprising one or more rare ginsenosides selected from the group: Rg6, Rh4, Rg3, PPT, Rk1, Rg5, Rh2, Rh3 and PPD, at respective daily effective doses. Preferably the composition comprises a daily effective dose of Rg6 of at least 0.1 mg and at most 35 mg. Preferably the composition comprises a daily effective dose of Rh4 of at least 20 mg and at most 85 mg. Preferably the composition comprises a daily effective dose of Rg3 of at least 5 mg and at most 50 mg. Preferably the composition comprises a daily effective dose of PPT of at least 0.01 mg and at most 35 mg. Preferably the composition comprises a daily effective dose of Rk1 of at least 10 mg and at most 50 mg. Preferably the composition comprises a daily effective dose of Rg5 of at least 0.01 mg and at most 100 mg. Preferably the composition comprises a daily effective dose of Rh2 of at least 0.1 mg and at most 30 mg. Preferably the composition comprises a daily effective dose of Rh3 of at least 0.1 mg and at most 3 mg.

"Effective amount" as used herein, should be understood as an amount sufficient to produce a selected effect, such as alleviating symptoms of a disease or disorder. "Daily effective dose" as used herein, should be understood as the effective amount required daily by a subject.

In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amount of each compound may vary. The term "more effective" means that the selected effect is alleviated to a greater extent by one treatment relative to the second treatment to which it is being compared. Preferably, the composition comprising a rare ginsenoside, a ginsan and a gintonin according to the invention is provided in an effective amount to the subject and/or object in need thereof. Even more preferably, the main constituents of said composition are provided in the preferred ratios and/or daily effective doses.

According to illustrative embodiments, an active combination according to the invention can be administered to a patient or subject alone, or in combination with other agents, drugs or hormones or in pharmaceutical compositions mixed with excipient(s) or other pharmaceutically or cosmetically acceptable carriers. In one embodiment, the pharmaceutically acceptable carrier is pharmaceutically inert.

The composition may be administered daily at an effective dose for as many times as desired to achieve the sought effects. According to a preferred embodiment, said composition is administered for a period of at least two days, preferably at least five days. As is exemplified in FIG. 1, an optimal effect for the composition is obtained for a treatment of at least 5 days.

Stress

In a third aspect, the invention relates to a composition for use as a medicament. Preferably a medicament for treatment or prevention of stress in a subject. Preferably a medicament for treatment or prevention of stress in a subject whereby the cognitive performance of said subject is improved. Preferably, for said purpose, the composition is provided in a pharmaceutically or cosmetically acceptable carrier. Preferably, for said purpose, the composition is provided in one or more pharmaceutically acceptable excipients.

In a sixth aspect, the invention relates to a method for treatment or prevention of stress in a subject. The method comprising the step of administering, to the subject, a composition according to a first aspect and/or a composition according to a second aspect.

In accordance with the present invention, a composition comprising a rare ginsenoside, a ginsan and a gintonin as disclosed herein is used for treatment of stress in a subject in need thereof. Use of the present composition for treatment of stress includes prophylactic use.

Stress is a state of the organism which is characterized by a specific syndrome (increased sympathetic activity, increased secretion of catecholamines, elevated blood pressure etc.) and can be triggered by a variety of unspecific stimuli (infections, injuries, burns, radiation effects and also anger, joy, pressure to perform and other factors). Stress can also be understood as external influences to which the body is not adequately adapted e.g. operations, poisoning, pregnancy (anon., Pschyrembel-"Klinisches Wörterbuch, 1990, Walter de Gruyter, Berlin-New York (1990)).

Stress can generally be described as environmental processes which trigger processes in the body through perceptual impulses where eustress is understood as excitatory influences having a positive effect and distress is understood as destructive influences having a negative effect. One effect of stress in a subject is a cognitive impairment of said subject.

Humans react to distress with headaches, sleeplessness, heart complaints, gastric complaints, diarrhoea, skin irritation, allergies, tenseness and/or cramps. Typical psychic stress reactions are nervous unrest, irritability, lack of concentration and sleep disorders. The stress hormones cortisone and ACTH (adrenocorticotrophic hormone) are mainly responsible for these reactions. Studies have shown that *ginseng* constituents regulate concentrations of cortisol and corticosteroids. Other studies have shown the immunostimulatory action of certain *ginseng* constituents. Thus, *ginseng* constituents have a calming effect, control stress hormones and control immune stimulator activity.

Without being bound to any mechanistic theories, it is rationalized that such compositions exhibit said stress treating and/or preventing performance due to an improved adaptogenic effect.

Without being bound to any mechanistic theories, it is rationalized that such compositions exhibit said stress treating and/or preventing performance due to an improved regulation of cortisol and corticosteroids concentrations and/or an improved immunostimulatory action.

In an especially preferred embodiment, the invention relates to a composition for use as a medicament for treatment or prevention of stress in a subject. Preferably, a medicament for treatment or prevention of stress in a subject whereby the cognitive performance of said subject is improved.

Without being bound to any mechanistic theories, it is rationalized that by improving the stress level of a subject, the cognitive performance of said subject is improved and vice versa. It is especially rationalized that these effects are caused by an improved adaptogenic effect.

The method for treatment or prevention of stress in a subject comprises at least the step of administering the composition to a subject. The composition may be administered to a subject in an effective amount according to any method known in the art. Preferably, the composition is formulated for oral administration. The composition may be administered to a subject in the form of a tablet, a lozenge, a pill, a capsule, a hard gelatine capsule, etc. Preferably, the composition is enclosed in a capsule suitable for oral administration to a subject. A daily effective dose of the composition may be administered in 1, 2, 3, 4, 5, 6, 7, 8, 9, 10, 11, 12, 13, 14, 15, 16, 17, 18, 19 and 20 different doses. Preferably, a daily effective dose is at most administered in five different doses. More preferably, a daily effective dose is administered in two different doses. Preferably, one of said two different doses is administered after breakfast. Preferably, one of said two different doses is administered after dinner. More preferably, a daily effective dose is administered in one dose. Said one dose preferably being administered after breakfast.

A daily effective dose of ginsenoside and rare ginsenoside in the composition is preferably at least 1 mg, more preferably at least 1 mg and at most 150 mg, even more preferably at least 10 mg and at most 100 mg, even more preferably at least 15 mg and at most 75 mg, even more preferably at least 20 mg and at most 55 mg, even more preferably at least 30 mg and at most 45 mg and most preferably about 37.5 mg.

A daily effective dose of rare ginsenoside in the composition is preferably at least 1 mg, more preferably at least 1 mg and at most 100 mg, even more preferably at least 10 mg and at most 80 mg, even more preferably at least 15 mg and at most 70 mg, even more preferably at least 20 mg and at most 60 mg, even more preferably at least 25 mg and at most 50 mg and most preferably about 30 mg.

A daily effective dose of ginsenoside in the composition is preferably at least 1 mg, more preferably at least 1 mg and at most 100 mg, even more preferably at least 2.5 mg and at most 75 mg, even more preferably at least 5 mg and at most 50 mg, even more preferably at least 5 mg and at most 30 mg, even more preferably at least 6 mg and at most 15 mg and most preferably about 7.5 mg.

A daily effective dose of ginsan and gintonin in the composition is preferably at least 1 mg, more preferably at least 1 mg and at most 35 mg, even more preferably at least 2 mg and at most 33 mg, even more preferably at least 4 mg and at most 31 mg, even more preferably at least 6 mg and at most 29 mg, even more preferably at least 8 mg and at most 24 mg and most preferably about 16 mg.

A daily effective dose of ginsan in the composition is preferably at least 0.3 mg, more preferably at least 0.3 mg and at most 30 mg, even more preferably at least 1 mg and at most 27 mg, even more preferably at least 5 mg and at most 25 mg, even more preferably at least 7 mg and at most 20 mg, even more preferably at least 10 mg and at most 17 mg and most preferably about 13 mg.

A daily effective dose of gintonin in the composition is preferably at least 0.1 mg, more preferably at least 0.1 mg and at most 10 mg, even more preferably at least 0.3 mg and at most 8 mg, even more preferably at least 0.5 mg and at most 7 mg, even more preferably at least 0.7 mg and at most 6 mg, even more preferably at least 1 mg and at most 5 mg and most preferably about 3 mg.

In an especially preferred embodiment, the composition comprises a combination of a rare ginsenoside, ginsan and gintonin at respective daily effective doses of about 32 mg rare ginsenoside, at least 10 and at most 16 mg ginsan and at least 1 mg and at most 5 mg gintonin. Preferably, at respective daily effective doses of about 32 mg rare ginsenoside, 13 mg ginsan and at least 1 mg and at most 5 mg gintonin. Preferably, at respective daily effective doses of about 32 mg rare ginsenoside, at least 10 and at most 16 mg ginsan and 3 mg gintonin. Most especially preferred, at respective daily effective doses of about 32 mg rare ginsenoside, 13 mg ginsan and 3 mg gintonin. The applicant notes the most more improved cognitive performance in a subject at such daily effective doses. This is for example substantiated in examples 1-21.

Preferably, the composition further also comprises a combination of compounds comprising a rare ginsenoside, ginsan and gintonin at a ratio of ginsan to rare ginsenoside of about 4:1 and a ratio of ginsan to gintonin of about 2:1, more preferably said composition further comprising a ratio of rare ginsenoside to ginsan of about 2.5:1, even more preferably said composition further comprising a ratio of rare ginsenoside to gintonin of about 10:1. As is exemplified in examples 1-21, the applicant notes the most improved cognitive performance in a subject at such ratios, especially when said ratios are provided at preferred daily effective doses as disclosed hereabove.

In an especially preferred embodiment, the present invention provides a composition comprising one or more rare ginsenosides selected from the group: Rg6, Rh4, Rg3, PPT, Rk1, Rg5, Rh2, Rh3 and PPD, at respective daily effective doses. Preferably the composition comprises a daily effective dose of Rg6 of at least 0.1 mg and at most 35 mg. Preferably the composition comprises a daily effective dose of Rh4 of at least 20 mg and at most 85 mg. Preferably the composition comprises a daily effective dose of Rg3 of at least 5 mg and at most 50 mg. Preferably the composition comprises a daily effective dose of PPT of at least 0.01 mg and at most 35 mg. Preferably the composition comprises a daily effective dose of Rk1 of at least 10 mg and at most 50 mg. Preferably the composition comprises a daily effective dose of Rg5 of at least 0.01 mg and at most 100 mg. Preferably the composition comprises a daily effective dose of Rh2 of at least 0.1 mg and at most 30 mg. Preferably the composition comprises a daily effective dose of Rh3 of at least 0.1 mg and at most 3 mg.

In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amount of each compound may vary. The term "more effective" means that the selected effect is alleviated to a greater extent by one treatment relative to the second treatment to which it is being compared. Preferably, the composition comprising a rare ginsenoside, a ginsan and a gintonin according to the invention is provided in an effective amount to the subject and/or object in need thereof. Even more preferably, the main constituents of said composition are provided in the preferred ratios and/or daily effective doses.

According to illustrative embodiments, an active combination according to the invention can be administered to a patient or subject alone, or in combination with other agents, drugs or hormones or in pharmaceutical compositions mixed with excipient(s) or other pharmaceutically or cosmetically acceptable carriers. In one embodiment, the pharmaceutically acceptable carrier is pharmaceutically inert.

The composition may be administered daily at an effective dose for as many times as desired to achieve the sought effects. According to a preferred embodiment, said composition is administered for a period of at least two days, preferably at least five days. As is exemplified in FIG. 1, an optimal effect for the composition is obtained for a treatment of at least 5 days.

Skin and/or Dermatological Disease

In a fourth aspect, the invention relates to the composition for use as a medicament. Preferably, for said use, the composition is provided in a pharmaceutically carrier.

Preferably, for said use, the composition is provided in a cosmetically acceptable carrier. Preferably the medicament, for use in treatment and/or prevention of a skin and/or dermatological disease.

In a seventh aspect, the invention relates to a method for improving skin conditions in a subject. The method comprising the step of administering, to the subject, a composition according to a first aspect and/or a composition according to a second aspect. Preferably the method, for use in treatment and/or prevention of a skin and/or dermatological disease.

In accordance with the present invention, a composition comprising a rare ginsenoside, a ginsan and a gintonin as disclosed herein is used for improving skin conditions in a subject. Said composition may also be used for treatment of a skin and/or dermatological disease. Preferably, said skin and/or dermatological disease being related to an inflammation, an allergic reaction, a contact hypersensitivity reaction or intolerance, an excessive sebaceous secretion, an exfoliation or a microbial dysbiosis. Preferably, said skin and/or dermatological disease is related to the epidermis. Use of the present composition includes prophylactic use.

Preferably, improving of the skin conditions of a subject or a subject in need thereof is at least one of a skin moisturization, a skin whitening, a wrinkle reduction or an anti-aging.

"Skin moisturization" as used herein, should be understood as a synonym for the terms "skin hydration", "skin absorption" or "skin adsorption" and refers generally to methods for improving the skin's absorptive and/or adsorptive capacity for water. As used herein the terms "absorb" or "absorption" broadly mean absorption of water into the skin, in particular into the epidermis and more particularly into the stratum corneum. As used herein the terms "adsorb" or "adsorption" broadly mean adsorption of water onto the skin, particularly onto the proteins of the epidermis and more particularly of the stratum corneum.

"Skin whitening" as used herein, should be understood as a synonym for the terms "skin lightening", "skin brightening" or "skin bleaching" and refers generally to methods for lightening, brightening, whitening, and/or evening of the skin tone, skin colour, and/or shade of skin, and/or to the reduction in sallowness, and/or to the lightening and/or fading of hyperpigmented marks and/or lesions including, but not limited to, pigmented spots, melanin spots, age spots, sun spots, senile lentigos, freckles, lentigos simplex, pigmented solar keratosis, seborrheic keratosis, melasma, acne marks, post-inflammatory hyperpigmentation, lentigines, ephelides, combinations of two or more thereof and the like.

"Wrinkle reduction" as used herein, should be understood as a synonym for the terms "wrinkle minimalization" and refers generally to methods for treating, including preventing, reducing, ameliorating, and/or eliminating, signs of dermatological aging, for example, wrinkles, fine lines, folds and furrows in the skin. More in particular, "wrinkle reduction" relates to treating or reducing hyperhidrosis and/or improving the aesthetic appearance of the skin of a subject.

"Anti-aging" as used herein, generally refers to methods for treating skin changes, such as skin aging and, in particular, aging induced by oxidative or degenerative processes. In particular, "anti-aging" as used herein, refers to methods for treating symptoms of skin aging including rhytids, wrinkles, jowls, sun damage, dull appearance of skin, sagging skin, keratosis, hyperpigmentation, melasma, solar lentigo, solar keratoses, dermatophilosis, or other skin discoloration disorders associated with aging.

Without being bound to any mechanistic theories, it is rationalized that the compositions exhibit said skin condition improving performance due to an improved adaptogenic effect. Without being bound to any mechanistic theories, it is rationalized that the compositions exhibit said medical or therapeutic effect in treating and/or preventing a skin and/or dermatological disease in a subject due to an improved adaptogenic effect.

Improving skin conditions and/or treatment or prevention of a skin and/or dermatological disease in a subject comprises at least the step of administering the composition to a subject. The composition may be administered to a subject in an effective amount according to any method known in the art.

In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amount of each compound may vary. The term "more effective" means that the selected effect is alleviated to a greater extent by one treatment relative to the second treatment to which it is being compared. Preferably, the composition comprising a rare ginsenoside, a ginsan and a gintonin according to the invention is provided in an effective amount to the subject and/or object in need thereof. Even more preferably, the main constituents of said composition are provided in the preferred ratios and/or daily effective doses.

The composition as disclosed herein may be administered orally. Preferably, the composition is formulated for oral administration.

The composition may be administered to a subject in the form of a tablet, a lozenge, a pill, a capsule, a hard gelatine capsule, etc. Preferably, the composition is enclosed in a capsule suitable for oral administration to a subject. A daily effective dose of the composition may be administered in 1, 2, 3, 4, 5, 6, 7, 8, 9, 10, 11, 12, 13, 14, 15, 16, 17, 18, 19 and 20 different doses. Preferably, a daily effective dose is at most administered in five different doses. More preferably, a daily effective dose is administered in two different doses. Preferably, one of said two different doses is administered after breakfast. Preferably, one of said two different doses is administered after dinner. More preferably, a daily effective dose is administered in one dose. Said one dose preferably being administered after breakfast.

A daily effective dose of ginsenoside and rare ginsenoside in the composition is preferably at least 1 mg, more preferably at least 1 mg and at most 150 mg, even more preferably at least 10 mg and at most 100 mg, even more preferably at least 15 mg and at most 75 mg, even more preferably at least 20 mg and at most 55 mg, even more preferably at least 30 mg and at most 45 mg and most preferably about 37.5 mg.

A daily effective dose of rare ginsenoside in the composition is preferably at least 1 mg, more preferably at least 1 mg and at most 100 mg, even more preferably at least 10 mg and at most 80 mg, even more preferably at least 15 mg and at most 70 mg, even more preferably at least 20 mg and at most 60 mg, even more preferably at least 25 mg and at most 50 mg and most preferably about 30 mg.

A daily effective dose of ginsenoside in the composition is preferably at least 1 mg, more preferably at least 1 mg and at most 100 mg, even more preferably at least 2.5 mg and at most 75 mg, even more preferably at least 5 mg and at most 50 mg, even more preferably at least 5 mg and at most 30 mg, even more preferably at least 6 mg and at most 15 mg and most preferably about 7.5 mg.

A daily effective dose of ginsan and gintonin in the composition is preferably at least 1 mg, more preferably at least 1 mg and at most 35 mg, even more preferably at least 2 mg and at most 33 mg, even more preferably at least 4 mg and at most 31 mg, even more preferably at least 6 mg and at most 29 mg, even more preferably at least 8 mg and at most 24 mg and most preferably about 16 mg.

A daily effective dose of ginsan in the composition is preferably at least 0.3 mg, more preferably at least 0.3 mg and at most 30 mg, even more preferably at least 1 mg and at most 27 mg, even more preferably at least 5 mg and at most 25 mg, even more preferably at least 7 mg and at most 20 mg, even more preferably at least 10 mg and at most 17 mg and most preferably about 13 mg.

A daily effective dose of gintonin in the composition is preferably at least 0.1 mg, more preferably at least 0.1 mg and at most 10 mg, even more preferably at least 0.3 mg and at most 8 mg, even more preferably at least 0.5 mg and at most 7 mg, even more preferably at least 0.7 mg and at most 6 mg, even more preferably at least 1 mg and at most 5 mg and most preferably about 3 mg.

Preferably, the composition further comprises a combination of compounds comprising a rare ginsenoside, ginsan and gintonin at a ratio of ginsan to rare ginsenoside of about 4:1 and a ratio of ginsan to gintonin of about 2:1, more preferably said composition further comprising a ratio of rare ginsenoside to ginsan of about 2.5:1, even more preferably said composition further comprising a ratio of rare ginsenoside to gintonin of about 10:1.

In an especially preferred embodiment, the composition comprises a combination of a rare ginsenoside, ginsan and gintonin at respective daily effective doses of about 32 mg rare ginsenoside, at least 10 and at most 16 mg ginsan and at least 1 mg and at most 5 mg gintonin. Preferably, at respective daily effective doses of about 32 mg rare ginsenoside, 13 mg ginsan and at least 1 mg and at most 5 mg gintonin. Preferably, at respective daily effective doses of about 32 mg rare ginsenoside, at least 10 and at most 16 mg ginsan and 3 mg gintonin. Most especially preferred, at respective daily effective doses of about 32 mg rare ginsenoside, 13 mg ginsan and 3 mg gintonin.

In an especially preferred embodiment, the present invention provides a composition comprising one or more rare ginsenosides selected from the group: Rg6, Rh4, Rg3, PPT, Rk1, Rg5, Rh2, Rh3 and PPD, at respective daily effective doses. Preferably the composition comprises a daily effective dose of Rg6 of at least 0.1 mg and at most 35 mg. Preferably the composition comprises a daily effective dose of Rh4 of at least 20 mg and at most 85 mg. Preferably the composition comprises a daily effective dose of Rg3 of at least 5 mg and at most 50 mg. Preferably the composition comprises a daily effective dose of PPT of at least 0.01 mg and at most 35 mg. Preferably the composition comprises a daily effective dose of Rk1 of at least 10 mg and at most 50 mg. Preferably the composition comprises a daily effective dose of Rg5 of at least 0.01 mg and at most 100 mg. Preferably the composition comprises a daily effective dose of Rh2 of at least 0.1 mg and at most 30 mg. Preferably the composition comprises a daily effective dose of Rh3 of at least 0.1 mg and at most 3 mg.

The composition as disclosed herein may be administered topically. Preferably, the composition is formulated for topical administration.

In the context of a composition for topical administration, "administration" and "application" are used interchangeably herein.

The composition for topical administration comprises a *ginseng* agent. The *ginseng* agent comprises a rare ginsenoside, a ginsan, a gintonin and optionally a ginsenoside and/or other ginsenoside constituents. Preferably, at ratios of the *ginseng* agent constituents as defined herein.

Preferably, the composition for topical administration comprises at least 0.001 wt. % *ginseng* agent by weight of the composition, more preferably at least 0.001 wt. %, more preferably at least 0.005 wt. %, more preferably at least 0.01 wt. %, more preferably at least 0.025 wt. %, more preferably at least 0.05 wt. %, more preferably at least 0.1 wt. %. Preferably, the composition for topical administration comprises at most 10 wt. % *ginseng* agent by weight of the composition, more preferably at most 5 wt. %, more preferably at most 4 wt. %, more preferably at most 3 wt. %, more preferably at most 1 wt. %, more preferably at most 0.5 wt. %. The lower limit of the *ginseng* agent is preferably 0.001 wt. % or more from the viewpoint that a sufficient improvement in skin conditions can be achieved according to the current invention. The upper limit of the *ginseng* agent is preferably 10 wt. % or less from the viewpoint of handleability.

Preferably, the *ginseng* agent comprised by the composition for topical administration comprises at least 1 wt. % of rare ginsenoside, ginsan and gintonin by weight of *ginseng* agent, more preferably at least 2 wt. %, more preferably at least 3 wt. %, more preferably at least 4 wt. %, more preferably at least 5 wt. %, more preferably at least 6 wt. %, more preferably at least 7 wt. %, more preferably at least 8 wt. %, more preferably at least 9 wt. %, more preferably at least 10 wt. %. Preferably, the *ginseng* agent comprised by the composition for topical administration comprises at most 30 wt. % of rare ginsenoside, ginsan and gintonin by weight of *ginseng* agent, more preferably at most 28 wt. %, more preferably at most 26 wt. %, more preferably at most 24 wt. %, more preferably at most 22 wt. %, more preferably at most 20 wt. %, more preferably at most 18 wt. %, more preferably at most 16 wt. %, more preferably at most 14 wt. %. The lower limit of rare ginsenoside, ginsan and gintonin by weight of *ginseng* agent is 1 wt. % or more from the viewpoint that a sufficient improvement in skin conditions can be achieved according to the current invention. The upper limit of the *ginseng* agent is preferably 30 wt. % or less from the viewpoint of commercial production and extraction processes. Ideally, the *ginseng* agent comprised by the composition for topical administration comprises about 12 wt. % of rare ginsenoside, ginsan and gintonin by weight of *ginseng* agent. Such concentration is preferred from an economic perspective.

The composition for topical administration may be administered to a subject in the form of a cream, a lotion, a spray, an ointment, a gel, a powdered mask, a skin patch, a paste, a cleanser, a foundation, etc. Preferably, the composition is administered in the form of a cream, a lotion or a spray suitable for topical administration to a subject. A daily effective dose of the composition may be applied in 1, 2, 3, 4, 5, 6, 7, 8, 9, 10, 11, 12, 13, 14, 15, 16, 17, 18, 19 and 20 different topical doses. Preferably, a daily effective dose is at most applied in five different topical doses. More preferably, a daily effective dose is applied in two different topical doses. Preferably, one of said two different topical doses is applied in the morning. Preferably, one of said two different doses is applied in the evening. More preferably, a daily effective dose is applied in one dose. Said one dose preferably being applied in the morning. Said one dose preferably being applied in the evening.

A daily effective dose of *ginseng* agent in a topically administered composition is preferably applied at a concentration of at least 0,0001 mg/cm$^2$ to the skin of a subject, more preferably at least 0,0001 mg/cm$^2$ and at most 2 mg/cm$^2$. More preferably, the *ginseng* agent is applied at a concentration of at least 0,0005 mg/cm$^2$, even more preferably at least 0,001 mg/cm$^2$, even more preferably at least 0,005 mg/cm$^2$, even more preferably at least 0.01 mg/cm$^2$. More preferably, the *ginseng* agent is applied at a concentration of at most 1.5 mg/cm$^2$, even more preferably at most 1.0 mg/cm$^2$, even more preferably at most 0.5 mg/cm$^2$, even more preferably at most 0.03 mg/cm$^2$. A *ginseng* agent applied at a concentration lower than 0,0001 mg/cm$^2$ is to diluted to exhibit skin condition improving properties according to the invention. A *ginseng* agent applied at a concentration higher than 2 mg/cm$^2$, may irritate the skin of a subject.

A daily effective dose of ginsenoside and rare ginsenoside in a topically administered composition is preferably applied at a concentration of at least 0.001 mg/cm$^2$ to the skin of a subject, more preferably at least 0,001 mg/cm$^2$ and at most 0.1 mg/cm$^2$. More preferably, the ginsenoside and rare ginsenoside are applied at a concentration of at least 0.002 mg/cm$^2$, even more preferably at least 0.004 mg/cm$^2$, even more preferably at least 0.006 mg/cm$^2$, even more preferably at least 0.008 mg/cm$^2$, even more preferably at least 0.01 mg/cm$^2$, even more preferably at least 0.012 mg/cm$^2$, even more preferably at least 0.014 mg/cm$^2$. More preferably, the rare ginsenoside is applied at a concentration of at most 0.1 mg/cm$^2$, even more preferably at most 0.08 mg/cm$^2$, even more preferably at most 0.06 mg/cm$^2$, even more preferably at most 0.04 mg/cm$^2$, even more preferably at most 0.02 mg/cm$^2$, even more preferably at most 0.018 mg/cm$^2$.

A daily effective dose of rare ginsenoside in a topically administered composition is preferably applied at a concentration of at least 0.001 mg/cm$^2$ to the skin of a subject, more preferably at least 0,001 mg/cm$^2$ and at most 0.1 mg/cm$^2$. More preferably, the rare ginsenoside is applied at a concentration of at least 0.002 mg/cm$^2$, even more preferably at least 0.004 mg/cm$^2$, even more preferably at least 0.006 mg/cm$^2$, even more preferably at least 0.008 mg/cm$^2$, even more preferably at least 0.01 mg/cm$^2$, even more preferably at least 0.011 mg/cm$^2$. More preferably, the rare ginsenoside is applied at a concentration of at most 0.1 mg/cm$^2$, even more preferably at most 0.08 mg/cm$^2$, even more preferably at most 0.06 mg/cm$^2$, even more preferably at most 0.04 mg/cm$^2$, even more preferably at most 0.02 mg/cm$^2$, even more preferably at most 0.015 mg/cm$^2$.

A daily effective dose of ginsenoside in a topically administered composition is preferably applied at a concentration of at least 0.0001 mg/cm$^2$ to the skin of a subject, more preferably at least 0,0001 mg/cm$^2$ and at most 0.01 mg/cm$^2$. More preferably, the ginsenoside is applied at a concentration of at least 0.0002 mg/cm$^2$, even more preferably at least 0.0004 mg/cm$^2$, even more preferably at least 0.0006 mg/cm$^2$, even more preferably at least 0.0008 mg/cm$^2$, even more preferably at least 0.001 mg/cm$^2$, even more preferably at least 0.002 mg/cm$^2$. More preferably, the ginsenoside is applied at a concentration of at most 0.01 mg/cm$^2$, even more preferably at most 0.008 mg/cm$^2$, even more preferably at most 0.006 mg/cm$^2$, even more preferably at most 0.005 mg/cm$^2$, even more preferably at most 0.004.

A daily effective dose of ginsan and gintonin in a topically administered composition is preferably applied at a concentration of at least 0.0001 mg/cm$^2$ to the skin of a subject, more preferably at least 0,0001 mg/cm$^2$ and at most 0.01 mg/cm$^2$. More preferably, the ginsan and gintonin are applied at a concentration of at least 0.0002 mg/cm$^2$, even more preferably at least 0.0004 mg/cm$^2$, even more preferably at least 0.0006 mg/cm$^2$, even more preferably at least 0.0008 mg/cm$^2$, even more preferably at least 0.001 mg/cm$^2$, even more preferably at least 0.002 mg/cm$^2$, even more preferably at least 0.004 mg/cm$^2$, even more preferably at least 0.006 mg/cm$^2$. More preferably, the ginsan and gintonin are applied at a concentration of at most 0.01 mg/cm$^2$, even more preferably at most 0.009 mg/cm$^2$, even more preferably at most 0.008 mg/cm$^2$, even more preferably at most 0.007 mg/cm$^2$.

A daily effective dose of ginsan in a topically administered composition is preferably applied at a concentration of at least 0.0001 mg/cm$^2$ to the skin of a subject, more preferably at least 0,0001 mg/cm$^2$ and at most 0.01 mg/cm$^2$. More preferably, the ginsan is applied at a concentration of at least 0.0002 mg/cm$^2$, even more preferably at least 0.0004 mg/cm$^2$, even more preferably at least 0.0006 mg/cm$^2$, even more preferably at least 0.0008 mg/cm$^2$, even more preferably at least 0.001 mg/cm$^2$, even more preferably at least 0.002 mg/cm$^2$, even more preferably at least 0.004 mg/cm$^2$, even more preferably at least 0.005 mg/cm$^2$. More preferably, the ginsan is applied at a concentration of at most 0.01 mg/cm$^2$, even more preferably at most 0.009 mg/cm$^2$, even more preferably at most 0.008 mg/cm$^2$, even more preferably at most 0.007 mg/cm$^2$, even more preferably at most 0.006 mg/cm$^2$.

A daily effective dose of gintonin in a topically administered composition is preferably applied at a concentration of at least 0.0001 mg/cm$^2$ to the skin of a subject, more preferably at least 0,0001 mg/cm$^2$ and at most 0.01 mg/cm$^2$. More preferably, the gintonin is applied at a concentration of at least 0.0002 mg/cm$^2$, even more preferably at least 0.0004 mg/cm$^2$, even more preferably at least 0.0006 mg/cm$^2$, even more preferably at least 0.0007 mg/cm$^2$, even more preferably at least 0.0008 mg/cm$^2$, even more preferably at least 0.0009 mg/cm$^2$, even more preferably at least 0.001 mg/cm$^2$, even more preferably at least 0.0011 mg/cm$^2$. More preferably, the gintonin is applied at a concentration of at most 0.01 mg/cm$^2$, even more preferably at most 0.008 mg/cm$^2$, even more preferably at most 0.006 mg/cm$^2$, even more preferably at most 0.004 mg/cm$^2$, even more preferably at most 0.002 mg/cm$^2$.

Preferably, the composition for topical administration further comprises a combination of compounds comprising a rare ginsenoside, ginsan and gintonin at a ratio of ginsan to rare ginsenoside of about 4:1 and a ratio of ginsan to gintonin of about 2:1, more preferably said composition further comprising a ratio of rare ginsenoside to ginsan of about 2.5:1, even more preferably said composition further comprising a ratio of rare ginsenoside to gintonin of about 10:1.

A daily effective dose of *ginseng* agent in a topically administered composition is preferably applied for at least 1 minute to the skin of a subject. More preferably, a daily effective dose of *ginseng* agent in a topically administered composition is preferably applied for at least 1 minute and at most 10 hours to the skin of a subject. A *ginseng* agent topically applied to the skin of a subject requires at least one minute to improve skin conditions. A *ginseng* agent topically applied for more than 10 hours is no longer effective and may irritate the skin of a subject. More preferably, a daily effective dose of *ginseng* agent in a topically administered composition is preferably applied for at least 5 minutes, even more preferably at least 10 minutes, even more preferably at least 15 minutes, even more preferably at least 20 minutes, even more preferably at least 25 minutes and even more preferably at least 30 minutes. More preferably, a daily effective dose of *ginseng* agent in a topically administered composition is preferably applied for at most 9 hours, even more preferably at most 9 hours, even more preferably at most 8 hours, even more preferably at most 7 hours and even more preferably at most 6 hours.

According to illustrative embodiments, an active combination according to the invention can be administered to a patient or subject alone, or in combination with other agents, drugs or hormones or in pharmaceutical compositions mixed with excipient(s) or other pharmaceutically or cosmetically acceptable carriers. In one embodiment, the pharmaceutically acceptable carrier is pharmaceutically inert.

The composition may be administered daily at an effective dose for as many times as desired to achieve the sought effects. According to a preferred embodiment, said composition is administered at a daily effective dose for a period of at least two days, preferably at least five days. The applicant notes that an optimal effect is obtained for a treatment of at least 5 days.

3. Preparation of a Composition of the Invention

In a eight aspect, the invention relates to a method for preparation of a medicament. Preferably a medicament for treatment or prevention of an impaired cognition in a subject in a subject. The composition preferably comprising a daily effective dose of rare ginsenoside of at least 1 mg and at most 100 mg. The composition preferably comprising a daily effective dose of ginsan of at least 0.3 mg and at most 30 mg. The composition preferably comprising a daily effective dose of gintonin of at least 0.1 mg and at most 10 mg. The method preferably comprising the step of growing a *ginseng* in a hydroponic environment. The method preferably comprising the step of harvesting a root from said grown *ginseng*. The method preferably comprising the step of grinding said harvested root to obtain said medicament. The method optionally also comprising a step of drying the harvested *ginseng* prior to grinding. The method optionally also comprising a step of cooking the grinded *ginseng*.

In a ninth aspect, the invention relates to a method according to a eighth aspect of the current invention for the production of a composition according to a first aspect for use as a medicament and/or a composition for use as a medicament according to a second aspect of the invention.

A hydroponic environment is a well-known technique for cultivating plants using mineral nutrient solutions, in water, without soil. Generally, over the earth surface plants may be grown with their roots in the mineral nutrient solution only or in an inert medium, such as perlite, gravel, mineral wool, expanded clay pebbles or coconut husk. In natural conditions, soil acts as a mineral nutrient reservoir but the soil itself is not essential to plant growth. When the mineral nutrients in the soil dissolve in water, plant roots are able to absorb them. When the required mineral nutrients are introduced into a plant's water supply artificially, soil is no longer required for the plant to thrive.

An advantage of hydroponics over conventional soil-based techniques is that the growing environment can be greatly controlled, in particular the nutrient level provided to the root environment. A further advantage is that water provided to the plants can be readily retained in the system providing significant water savings. A hydroponic environment is especially advantageous in view of the current invention, as the final constituent concentrations in the *ginseng* root system may be controlled by meticulously adjusting the nutrient level administered to the *ginseng* plant. The applicant notes that, to his knowledge, no other cultivating technique allows for growing a *ginseng* root with the necessary constituent ratios and concentrations for obtaining a composition according to the current invention, without the need of additional purifying steps. Moreover, as a consequence of the previously described advantages, the applicant notes that hydroponic cultivation of *ginseng* takes much less time compared to soil cultivation.

In an especially preferred embodiment, the method comprises the step of growing a *ginseng* in a controlled hydroponic environment. A controlled hydroponic environment is a technique for growing plants in nutrient solutions which are water containing fertilizers with or without the use of an artificial medium such as sand, gravel, vermiculite, rockwool, perlite, or sawdust to provide mechanical support in a technically controlled environment. Under these systems there is no other supporting medium for plant roots. Controlled hydroponic environments are advantageous as they allow for an even further controlled nutrient administration to the growing a *ginseng* plant.

In an especially preferred embodiment, the method comprises the step of growing a *ginseng* in an aseptic hydroponic environment. An aseptic hydroponic environment is a hydroponic technique performed under conditions of sufficient cleanliness to avoid the presence of microbes such as bacteria, yeasts, fungi and moulds but also insects and other pests. By using an aseptic hydroponic environment, the use of pesticides can be completely avoided.

It should, however, be clear to person skilled in the art, that the composition according to the current invention may be produced according to any method known in the art. For example, according to an alternative embodiment, the composition may be prepared by mixing aliquots each comprising one or more constituents of the composition.

Ginsenosides according to any of the methods and compositions described herein can be isolated and/or purified from a *ginseng, ginseng* extract or other plant source, or the ginsenoside can be a synthetic ginsenoside that is manufactured.

According to an especially preferred embodiment, the composition may be obtained by extracting the different composition constituents from a *ginseng*.

Preferably, prior to an extraction step, the root of a *ginseng* is dried. Preferably, prior to an extraction step, the root of a *ginseng* is grinded. Preferably, prior to an extraction step, the root of a *ginseng* is cooked. More preferably, prior to an extraction step, the root of a *ginseng* is dried, subsequently grinded and finally cooked. It should, however, be clear that drying and/or grinding and/or cooking the *ginseng* is not an absolute requirement for the extraction as disclosed herein. Grinding and/or drying *ginseng* increases efficacy of subsequent extractions steps. Cooking *ginseng* increases bioavailability of *ginseng* constituents.

According to a preferred embodiment, said rare ginsenoside, ginsenoside and gintonin are extracted from a *ginseng* using a hydroalcoholic extraction. Preferably, using two or more subsequent hydroalcoholic extractions. Between each of said hydroalcoholic extractions, a filtration step is provided. After said filtration step, a filtrate and a hydroalcoholic solution are obtained. The filtrate is rich in ginsan. The hydroalcoholic solution is rich in rare ginsenosides, ginsenosides and gintonin. The filtrate obtained by said filtration step is subjected to the subsequent hydroalcoholic extraction. The hydroalcoholic solution obtained by said filtration step is preferably collected.

Each of said subsequent hydroalcoholic extractions preferably comprising a mixing step. Each of said subsequent hydroalcoholic extractions preferably comprising a recirculation step. Preferably, each mixing and/or recirculation step for at least 30 minutes and at most 10 hours, more preferably at least 60 minutes and at most 8 hours, more preferably at least 90 minutes and at most 6 hours, more preferably at least 2 hours and at most 4 hours, most preferably about 2 hours 30 minutes.

The collected hydroalcoholic solution (i.e. the hydroalcoholic solution collected from said two or more subsequent hydroalcoholic extractions) can be subjected to a fractionation. "Fractionation" as used herein, refers to a substantial separation and recovery of a first fraction rich in rare ginsenoside and ginsenoside and a second fraction rich in gintonin. Preferably, said collected hydroalcoholic solution is subjected to a fractionation using an aqueous solution. After said fractionation, a water-soluble, a water-insoluble fraction and a water-insoluble precipitate fraction are obtained. The water-insoluble precipitate fraction is the gintonin-enriched fraction. The water-insoluble fraction is rich in rare ginsenosides and ginsenosides.

The collected hydroalcoholic solution (i.e. the hydroalcoholic solution collected from said two or more subsequent hydroalcoholic extractions) can be subjected to a concentration treatment. Preferably, said collected hydroalcoholic solution is subjected to a partial vacuum treatment. Preferably, said vacuum treatment at a pressure of at least 50 mbar, even more preferably at a pressure of at least 50 mbar and at most 500 mbar, even more preferably of at least 75 mbar and at most 250 mbar and most preferably of at least 100 mbar and at most 200 mbar. Preferably, said vacuum treatment at a temperature of at least 10° C., more preferably at least 20° C., even more preferably at least 30° C., even more preferably at least 40° C. and most preferably at about 50° C.

It should be clear, that any hydroalcohol may be used for the hydroalcoholic extraction of said rare ginsenoside, ginsenoside and gintonin. Preferably, ethanol is used because of its wide availability. Preferably, said hydroalcoholic extraction is performed at a temperature of at least 10° C. and at most 75° C. Cycle times increase substantially at temperatures below 10° C. Most hydroalcohols boil at temperatures above 75° C. More preferably, said hydroalcoholic extraction is performed at a temperature of at least 20° C. and at most 70° C., even more preferably at least 30° C. and at most 65° C., even more preferably at least 40° C. and at most 60° C., even more preferably at least 45° C. and at most 55° C., most preferably at about 55° C.

According to a specific embodiment, the hydroalcoholic extraction for extraction of said rare ginsenoside, ginsenoside and gintonin comprises two subsequent hydroalcoholic extractions. A first hydroalcoholic extraction can be performed under mixing and recirculation for 2 hours and 30 minutes using 35 l of 70% EtOH/30% H2O at 50° C. The extracted solution is filtered. The filtrate is subjected to a second hydroalcoholic extraction, which can be identical to the first. Additional specific embodiments are discussed in the examples.

According to a preferred embodiment, said rare ginsenoside, ginsenoside and gintonin are extracted using a hydroalcoholic extraction to obtain a filtrate. Said filtrate is rich in ginsan. Preferably, said filtrate is subsequently subjected to an aqueous extraction, more preferably two or more subsequent aqueous extractions. Between each of said subsequent aqueous extraction steps, a centrifugation step is provided. After said centrifugation step, a solid fraction and a liquid fraction are obtained. The solid fraction obtained by said centrifugation step is subjected to the subsequent aqueous extraction. The liquid fraction obtained by said centrifugation step is preferably collected.

An aqueous extraction, as disclosed herein, is effective for the additional extraction of the polysaccharide ginsan. Preferably, ginsan is extracted using two or more aqueous extractions. It should, however, be clear that ginsan might be obtained directly from *ginseng*, preferably using an aqueous extraction, preferably after drying and/or grinding and/or cooking of said *ginseng*.

Each aqueous extraction preferably comprising a mixing step. Preferably, said mixing step for at least 10 minutes and at most 6 hours, more preferably at least 30 minutes and at most 5 hours, more preferably at least 1 hour and at most 4 hours 30 minutes, more preferably at least 1 hour 30 minutes and at most 4 hours, more preferably at least 2 hours and at most 3 hours 30 minutes, most preferably about 2 hours 30 minutes.

It should be clear, that any aqueous solution may be used for this extraction. Preferably, said aqueous extraction is performed at a temperature of at least 60° C. and at most 100° C. Cycle times increase substantially at temperatures below 60° C. At temperatures above 100° C. aqueous solutions boil. More preferably, said hydroalcoholic extraction is performed at a temperature of at least 65° C. and at most 95° C., even more preferably at least 70° C. and at most 90° C., even more preferably at least 75° C. and at most 85° C., most preferably at about 80° C.

Preferably, after said mixing step, the mixture is heated to a temperature of at least 60° C. and at most 100° C. for at least 5 hours and at most 20 hours, preferably for about 16 hours. Cycle times increase substantially at temperatures below 60° C. At temperatures above 100° C. aqueous solutions boil. More preferably, said hydroalcoholic extraction is performed at a temperature of at least 65° C. and at most 95° C., even more preferably at least 70° C. and at most 90° C., even more preferably at least 75° C. and at most 85° C., most preferably at about 80° C.

The ginsan-rich obtained aqueous extract can be treated using dialysis. Preferably, prior to dialysis, the aqueous extract is concentrated using a vacuum evaporation. Preferably, said concentrate is dialysed for at least one day and at most 15 days against water. Preferably, said dialysis cutting of molecules with a molecular weight of at most 5 kDa, preferably at most 10 kDa and most preferably at most 15 kDa. To obtain a ginsan precipitate, a hydroalcoholic solution may be added.

The ginsan-rich obtained aqueous extract can be filtered. Preferably, said filtration comprising a filtration step with a mesh size of at least 1 μm and at most 30 μm, more preferably at least 5 μm and at most 25 μm, more preferably at least 10 μm and at most 20 μm and most preferably about 15 μm. Preferably, said filtration step using a filtration centrifuge. Preferably, said filtration comprising a filtration step with a mesh size of at least 0.1 μm and at most 1 μm, more preferably at least 0.10 μm and at most 0.90 μm, more preferably at least 0.25 μm and at most 0.75 μm and most preferably about 0.45 μm. Preferably, said filtration comprising a filtration step with a mesh size of at least 15 kDa and at most 25 kDa, more preferably at least 17 kDa and at most 23 kDa and most preferably about 20 kDa. Preferably, each of said filtration steps, disclosed hereabove, comprising 1, 2, 3, 4, 5, 6 or 7 subsequent cycles.

According to a specific embodiment, aqueous extraction of said ginsan comprises two subsequent aqueous extractions. A first aqueous extraction may be performed under mixing for 2 hours 30 min at 80° C. using 30 l of hot water. Subsequently, the mixing may be stopped and the resulting mixture can be heated to 80° C. for another 16 hours. The resulting water and solid fraction were separated by centrifugation. The solid fraction may be subsequently subjected to a second aqueous extraction, which can be identical to the first. Additional specific embodiments are discussed in the examples.

In further illustrative embodiments, the ginsenoside of the methods and compositions described herein is isolated and/or purified from a *ginseng* species belonging to the genus *Panax*, or a *ginseng* extract thereof. In further illustrative embodiments, the ginsenoside of the methods and compositions described herein is formulated as or forms part of a *ginseng* extract. *Ginseng* extracts can be obtained from plant materials. Plant materials can be extracted with water or an aqueous solution, an alcohol solution, or a combination of water and alcohol. Plant materials may also be extracted using supercritical means alone or in combination with extraction steps using water or alcohol or combination solutions. Ginsenosides can be isolated and/or purified from *ginseng* or another plant source using methods known in the art, which are disclosed, for example, in Chemistry and Pharmacology of Natural Products: Saponins, By K. Hostettmann, A. Marston, Cambridge University Press 1995, which is incorporated herein by reference.

In further illustrative embodiments, procedures for obtaining ginsenosides Rb1, Rb2, Rc and/or Rd typically comprise aqueous or organic extraction of one or more suitable *Panax* species, evaporating the extracted solution to dryness, followed by column chromatography, thin-layer chromatography, and/or high-performance chromatography to obtain a purified ginsenoside fraction. Techniques for the extraction and purification of plant extracts are known to the skilled artisan, and may be adapted for the preparation of each of or a mixture of one or more of Rb1, Rb2, Rc, or Rd, from techniques such as the ones disclosed in the following documents: U.S. Pat. Nos. 6,156,291, 6,083,932, 4,157,894, 5,137,878 and 5,230,889. Isolation and purification procedures for Rb1, Rb2, Rc and Rd are also described in, for example, Shibata et al., Economic and Medicinal Plant Research, World Scientific, Philadelphia pp. 217-284, 1985; U.S. Pat. No. 7,235,267, Kawashima et al., J. Med. Pharmacol. Soc. Wakan-Yaku 1986, 3, 235-236 and Oura et al., Journal of Biochemistry (Tokyo) 1975, 77(5), 1057-65.

In further illustrative embodiments, the ginsenoside of the compositions or methods described herein is a member of the dammarane family or the oleanane family. In further illustrative embodiments, the ginsenoside of the compositions or methods described herein is a member of a group selected from protopanaxadiols, protopanaxatriols, and pseudoginsenoside FI 1.

Traditionally, ginsenosides (including ginsenosides and rare ginsenosides as used herein) have a poor bioavailability. Ginsenosides are, however, easily metabolized or hydrolysed by intestinal bacteria into more bioavailable and active ginsenosides. "Ginsenoside" and "rare ginsenoside" as used herein, should also include any ginsenoside or rare ginsenosides metabolite that is a product of ginsenoside or rare ginsenoside metabolism by mammalian gut bacteria. Non-limiting examples of a ginsenoside metabolite include 20-b-O-glucopyranosyl-20(S)-protopanaxadiol and 20(S)-protopanaxadiol.

Bioavailability of rare ginsenosides, ginsenosides, ginsan and gintonin as well as other *ginseng* constituents, preferably ginsenosides, can be increased by cooking a harvested *ginseng* root. Preferably, said harvested root is cooked. More preferably, said harvested root is cooked after drying and/or grinding said harvested root. It should be clear to a person skilled in the art, that any cooking methodology known in the art can be used. The applicant notes the best retention of the different essential *ginseng* constituents upon steam cooking the harvested roots. Preferably, said harvested root is steam cooked. More preferably, said harvested root is steam cooked after drying and/or grinding said harvested root. More preferably, said harvested root is steam cooked at a temperature of at least 100° C. and at most 150° C., even more preferably at most 140° C., even more preferably at most 130° C. and even more preferably at most 121° C. More preferably, said harvested root is steam cooked for at least 30 minutes, even more preferably at least 30 minutes and at most 10 hours and even more preferably at least 1 hour and at most 6 hours.

In a further embodiment, the ginsenoside may also be a synthetic ginsenoside that is manufactured. Methods of manufacturing ginsenoside synthetically are known in the art and are disclosed, for example, in Organic Synthesis with Enzymes in Non-Aqueous Media, edited by Giacomo Carrea, Sergio Riva, Willey VCH 2008, which is incorporated herein by reference.

Ginsan may be isolated from any species of the *Panax* genus using any method known in the art. For example, as is disclosed by Kim et al. (1997), ginsan may be isolated from an ethanol insoluble fraction of a *ginseng* water extract (*Panax ginseng* C. A. Meyer, Araliaceae).

Gintonin may be obtained from any species of the *Panax* genus using any method known in the art. For example, as is disclosed EP 2 502 933, gintonin may be obtained by subsequently partitioning, fractioning and dialyzing a methanol extract obtained from any *ginseng*.

PREFERRED EMBODIMENTS OF THE INVENTION

1. In a first aspect, the invention relates to a composition for improving cognitive performance in a subject, said composition comprises a rare ginsenoside, a ginsan and a gintonin.
2. Composition according to the first aspect, wherein the ratio of ginsan to gintonin is at least 500:1 and at most 1:100.
3. Composition according to the first aspect, wherein the ratio of rare ginsenosides to ginsan and gintonin is at least 250:1 and at most 1:40.
4. Composition according to the first aspect, wherein the ratio of rare ginsenoside to ginsan is at least 300:1 and at most 1:30.
5. Composition according to the first aspect, wherein the ratio of rare ginsenoside to gintonin is at least 1000:1 and at most 1:10.
6. Composition according to the first aspect, wherein said rare ginsenoside is selected from the group comprising: C-K, Rg6, Rh4, Rg3, PPT, Rk1, Rg5, Rh2, Rh3 and PPD.
7. Composition according to the first aspect, wherein said rare ginsenoside comprises Rg5 and Rh2 and optionally one or more rare ginsenosides selected from the group comprising: C-K, Rg6, Rh4, Rg3, PPT, Rk1, Rh3 and PPD.
8. Composition according to the first aspect, wherein said rare ginsenoside comprises Rg5 and Rh2 and optionally one or more rare ginsenosides selected from the group comprising: C-K, Rg6, Rh4, Rg3, PPT, Rk1, Rh3 and PPD and wherein the ratio of a Rg5 and Rh2 to a total amount of rare ginsenoside is at least 1:1 and at most 1:4.
9. Composition according to the first aspect, wherein said composition further comprises a ginsenoside, preferably whereby said ginsenoside is selected from the group comprising: Rg1, Re, Rf, Rh1, Rg2, Rb1, Rc, Rb2 and Rd.
10. Composition according to the first aspect, wherein said composition further comprising a ginsenoside selected from the group comprising: Rg1, Re, Rf, Rh1, Rg2, Rb1, Rc, Rb2 and Rd and wherein the ratio of Rc to a total amount of rare ginsenoside and ginsenoside is at least 1:1 and at most 1:3.
11. Composition according to the first aspect, wherein the ratio of rare ginsenoside to ginsenoside is at least 200:1 and at most 1:5.
12. Composition according to the first aspect, wherein said composition further comprising a ginsenoside and wherein the ratio of one or more compounds selected from the group comprising: C-K, Rk1, Rh2, Rh3, Rh4, Rg2, Rg3 and Rg6 to a total amount of rare ginsenosides and ginsenosides in the composition is at least 1:4 and at most 1:1.
13. Composition according to the first aspect, whereby said composition is formulated for oral administration.
14. Composition according to the first aspect, whereby said composition is enclosed in a capsule for oral administration.
15. In a second aspect, the invention relates to a composition according to the first aspect, for use in treatment or prevention of an impaired cognition in a subject, preferably whereby the composition is provided in a pharmaceutically or cosmetically acceptable carrier.
16. Composition according to the second aspect, whereby the composition is provided in one or more pharmaceutically acceptable excipients.
17. In a third aspect, the invention relates to a composition according to the first aspect, whereby the composition is provided in a pharmaceutically or cosmetically acceptable carrier.

18. Composition according to the third aspect, whereby the composition is provided in one or more pharmaceutically acceptable excipients.
19. In a fourth aspect, the invention pertains to a composition according to the first aspect wherein said composition is provided in a pharmaceutically and/or cosmetically acceptable carrier.
20. Composition according to the fourth aspect, whereby the composition is provided in one or more pharmaceutically acceptable excipients.
21. Composition according to the fourth aspect, for use in treatment and/or prevention of a skin and/or dermatological disease.
22. Composition according to the fourth aspect, for use in treatment and/or prevention of a skin and/or dermatological disease, whereby said skin and/or dermatological disease is related to an inflammation, an allergic reaction, a contact hypersensitivity reaction or intolerance, an excessive sebaceous secretion, an exfoliation or a microbial dysbiosis, preferably of the epidermis.
23. In a fifth aspect, the invention relates to a method for improving cognitive performance in a subject, the method comprising the step of administering, to the subject, a composition according to a first aspect and/or a composition according to a second aspect.
24. Method according to the fifth aspect, for treatment or prevention of an impaired cognition in a subject
25. Method according to the fifth aspect, whereby said composition comprises a daily effective dose of rare ginsenoside of at least 1 mg and at most 100 mg.
26. Method according to the fifth aspect, whereby said composition comprises a daily effective dose of ginsan of at least 0.3 mg and at most 30 mg.
27. Method according to the fifth aspect, whereby said composition comprises a daily effective dose of gintonin of at least 0.1 mg and at most 10 mg.
28. In a sixth aspect, the invention relates to a method for treatment or prevention of stress in a subject, the method comprising the step of administering, to the subject, a composition according to a first aspect and/or a composition according to a second aspect.
29. Method according to the sixth aspect, whereby said composition comprises a daily effective dose of rare ginsenoside of at least 1 mg and at most 100 mg.
30. Method according to the sixth aspect, whereby said composition comprises a daily effective dose of ginsan of at least 0.3 mg and at most 30 mg.
31. Method according to the sixth aspect, whereby said composition comprises a daily effective dose of gintonin of at least 0.1 mg and at most 10 mg.
32. In a seventh aspect, the invention pertains to a method for improving skin conditions in a subject, the method comprising the step of administering, to the subject, a composition according to a first aspect and/or a second aspect.
33. Method according to the seventh aspect, for treatment and/or prevention of a skin and/or dermatological disease.
34. Method according to the seventh aspect, whereby the composition is administered topically.
35. Method according to the seventh aspect, whereby the composition is administered topically and wherein said composition comprises a ginsan and gintonin concentration of at least 10 wt. % and at most 50 wt. % by weight of said composition.
36. Method according to the third aspect, whereby the composition is administered topically and wherein said composition comprises a rare ginsenoside concentration of at least 60 wt. % and at most 90 wt. % by weight of said composition.
37. Method according to the seventh aspect, whereby the composition is administered topically and wherein said composition comprises a ginsan concentration of at least 10 wt. % and at most 35 wt. % by weight of said composition.
38. Method according to the seventh aspect, whereby the composition is administered topically and wherein said composition comprises a gintonin concentration of at least 1 wt. % and at most 10 wt. % by weight of said composition.
39. Method according to the third aspect, whereby the composition is administered orally.
40. Method according to the seventh aspect, whereby the composition is administered orally and whereby said composition comprises a daily effective dose of rare ginsenoside of at least 1 mg and at most 100 mg.
41. Method according to the seventh aspect, whereby the composition is administered orally and whereby said composition comprises a daily effective dose of ginsan of at least 0.3 mg and at most 30 mg.
42. Method according to the seventh aspect, whereby the composition is administered orally and whereby said composition comprises a daily effective dose of gintonin of at least 0.1 mg and at most 10 mg.
43. In a eighth aspect, the invention pertains to a method for treatment or prevention of an impaired cognition in a subject, for preparation of a medicament, preferably a medicament for treatment or prevention of an impaired cognition in a subject, and/or for preparation of a composition for improving skin conditions in a subject, said composition comprising a rare ginsenoside, a ginsan and a gintonin, the method comprising the steps of extracting each of said rare ginsenoside, said ginsan and said gintonin from a root of a grown *ginseng*.
44. Method according to the eighth aspect, whereby said root is grown in a hydroponic environment.
45. Method according to the eighth aspect, whereby said root is grown in a controlled hydroponic environment.
46. Method according to the eighth aspect, whereby said root is grown in a aseptic hydroponic environment.
47. Method according to the eighth aspect, whereby said rare ginsenoside is extracted using a hydroalcoholic extraction.
48. Method according to the eighth aspect, whereby said ginsan is extracted using an aqueous extraction.
49. Method according to the eighth aspect, whereby said gintonin is extracted using a hydroalcoholic extraction.
50. Method according to the eighth aspect, whereby said rare ginsenoside and gintonin are extracted using a hydroalcoholic extraction and whereby a resulting hydroalcoholic extract is filtered to obtain a filtrate.
51. Method according to the eighth aspect, whereby said gintonin is extracted from said filtrate using an aqueous extraction.
52. Method according to the eighth aspect, whereby said resulting hydroalcoholic extract is subjected to a fractionation to obtain said gintonin.
53. Method according to the eighth aspect, whereby extracts of rare ginsenoside, ginsan and gintonin are aliquoted to the composition.
54. Method according to the eighth aspect, for preparation of a medicament, preferably a medicament, for treatment or prevention of an impaired cognition in a subject, the medicament comprising: a daily effective dose of rare ginsenoside of at least 1 mg and at most 100 mg; a daily effective dose of ginsan of at least 0.3 mg and at most 30 mg; and a daily effective dose of gintonin of at least 0.1 mg and at most 10 mg, the method comprising the steps of: growing a *ginseng* in a hydroponic environment; harvesting a root from said grown *ginseng*; and grinding said harvested root to obtain said medicament.

55. Method according to the eighth aspect, for preparation of a medicament, preferably a medicament, for treatment or prevention of stress in a subject, the medicament comprising: a daily effective dose of rare ginsenoside of at least 1 mg and at most 100 mg; a daily effective dose of ginsan of at least 0.3 mg and at most 30 mg; and a daily effective dose of gintonin of at least 0.1 mg and at most 10 mg, the method comprising the steps of: growing a *ginseng* in a hydroponic environment; harvesting a root from said grown *ginseng*; and grinding said harvested root to obtain said medicament.

56. In a ninth aspect, the invention relates to a method according to the fourth aspect for preparation of a composition according to the first aspect for use as a medicament and/or a composition for use as a medicament according to the second aspect.

57. In a tenth aspect, the invention relates to a kit comprising one or more aliquots of a composition, said composition comprising a rare ginsenoside, a ginsan and a gintonin.

58. Kit according to the tenth aspect, whereby said composition is a composition according to the first aspect and/or a composition according the second aspect.

EXAMPLES

In the following, examples are intended to further clarify the present invention and are nowhere intended to limit the scope of the present invention.

Examples 1-21

A simple composition according to the current invention comprises a rare ginsenoside, a ginsan and a gintonin. Table 1 provides an overview of simple compositions according to the invention. Table 2 provides an overview of compositions according to the invention comprising ginsenosides. Table 3 provides an overview of compositions according to the invention also comprising an additional ingredient, an additive, a carrier and/or an excipient. Throughout the examples, these constituents will be addressed as additional ingredients unless otherwise specified.

TABLE 1

Simple compositions.

| example | rare ginsenoside | ginsan | gintonin |
|---|---|---|---|
| 1 | 32 mg | 13 mg | 3 mg |
| 2 | 35 mg | 11 mg | 4 mg |
| 3 | 29 mg | 15 mg | 2 mg |
| 4 | 70 mg | 5 mg | 5 mg |
| 5 | 30 mg | 10 mg | 7 mg |
| 6 | 90 mg | 1 mg | 0.5 mg |
| 7 | 10 mg | 25 mg | 9 mg |

TABLE 2

Compositions comprising ginsenosides.

| example | rare ginsenoside | ginsan | gintonin | ginsenoside |
|---|---|---|---|---|
| 8 | 1 mg | 30 mg | 10 mg | 15 mg |
| 9 | 100 mg | 0.3 mg | 0.1 mg | 0.5 mg |
| 10 | 20 mg | 25 mg | 9 mg | 0.4 mg |
| 11 | 80 mg | 1 mg | 0.5 mg | 60 mg |
| 12 | 32 mg | 13 mg | 3 mg | 6 mg |
| 13 | 37 mg | 11 mg | 2 mg | 4 mg |
| 14 | 37 mg | 15 mg | 4 mg | 5 mg |

TABLE 3

Compositions comprising an additional ingredient.

| example | rare ginsenoside | ginsan | gintonin | ginsenoside | additional ingredient | formulation |
|---|---|---|---|---|---|---|
| 15 | 32 mg | 13 mg | 3 mg | 5 mg | 32.4 mg brown sugar | 2 capsules of 50 mg. |
| 16 | 40 mg | 15 mg | 5 mg | 10 mg | 200 ml saline | Powdered composition of 106 mg for daily intake. Preferably dissolved in saline. |
| 17 | 31 mg | 12 mg | 4 mg | 6 mg | 500 mg alginic acid | 1 capsule for daily intake. Preferably after dinner. |
| 18 | 1 mg | 30 mg | 10 mg | 9 mg | 350 mg Arabic gum | 5 tablets of 100 mg for daily intake. |

TABLE 3-continued

| Compositions comprising an additional ingredient. | | | | | | |
|---|---|---|---|---|---|---|
| example | rare ginsenoside | ginsan | gintonin | ginsenoside | additional ingredient | formulation |
| 19 | 99 mg | 0.4 mg | 0.1 mg | 0.5 mg | 100 mg rice flour | 2 capsules of 100 mg for daily intake. |
| 20 | 20 mg | 25 mg | 9 mg | 15 mg | 5 mg dextrose dissolved in 30 cl water | Powdered composition for daily intake. Preferably dissolved in a dextrose solution. |
| 21 | 80 mg | 4.5 mg | 0.5 mg | 65 mg | 450 mg agar | Agar based dessert for daily intake. Preferably after dinner. |

Table 4 shows the results of testing the compositions for cognitive improvement in a patient at five days of intake. A detailed experimental setup for the performance of the compositions is provided in example 31. Examples 1-14 were administered daily enclosed in two capsules as specified in example 31. The retention of cognitive improvement was evaluated by repeating a d2 test of attention 24 hours after intake of the last dose compared to the baseline of the first day of treatment. The performance of the different compositions is force ranked in function of a positive and negative control. The positive and negative control were prepared as disclosed in example 31.

TABLE 4

| Performance examples 1-21. | | |
|---|---|---|
| example | cognitive improvement | retention cognitive improvement 24 h after treatment |
| 1 | +++** | +++ |
| 2 | +++ | +++ |
| 3 | +++ | +++ |
| 4 | + | + |
| 5 | +++ | + |
| 6 | + | + |
| 7 | + | + |
| 8 | * | ++ |
| 9 | * | ++ |
| 10 | + | ++ |
| 11 | * | ++ |
| 12 | +++** | ++ |
| 13 | +++ | +++ |
| 14 | +++ | ++ |
| 15 | +++** | +++ |
| 16 | ++ | +++ |
| 17 | +++ | +++ |
| 18 | * | + |
| 19 | * | * |
| 20 | ++ | * |
| 21 | + | * |

+++ Significantly better performance compared to negative control ($p < 0.0001$) and significantly better performance to positive control ($p < 0.001$).
++ Significantly better performance compared to negative control ($p < 0.001$) and significantly better performance to positive control ($p < 0.05$).
+ Significantly better performance compared to negative control ($p < 0.05$).
*Observably higher performance compared to positive and negative control (non-significant).
**Observably higher performance compared to other performance-groups (non-significant).

Example 22

A composition according to the current invention comprises a rare ginsenoside. A composition according to the current invention comprises may also comprise a ginsenoside. Table 5 provides an overview of the average ginsenoside profile of a composition according to the invention. Table 6 provides an overview of the average rare ginsenoside profile of a composition according to the invention. A duplicate sample (n=2) was collected from examples 1-21. All additional ingredients were purged from the samples. 42 samples were prepared and analysed in analogy with the methodology described in example 28.

TABLE 5

| Average ginsenoside profile. | | | |
|---|---|---|---|
| ginsenosides | mean (mg/g dry matter) | min (mg/g dry matter) | max (mg/g dry matter) |
| Rg1 | 0.02 | 0 | 0.63 |
| Re | 0.2 | 0 | 2.34 |
| Rf | 0.06 | 0 | 0.58 |
| Rh1 | 0.02 | 0 | 0.51 |
| Rg2 | 1.79 | 0 | 3.11 |
| Rb1 | 2.54 | 0 | 7.77 |
| Rc | 1.11 | 0 | 5.09 |
| Rb2 | 1.02 | 0 | 3.99 |
| Rd | 4.38 | 0 | 10.81 |

TABLE 6

| Average rare ginsenoside profile. | | | |
|---|---|---|---|
| rare ginsenosides | mean (mg/g dry matter) | min (mg/g dry matter) | max (mg/g dry matter) |
| Rg6 | 12.23 | 0 | 16.92 |
| Rh4 | 17.93 | 10.07 | 41.55 |
| Rg3 | 14.17 | 2.6 | 24.18 |
| PPT | 0.58 | 0 | 17.74 |
| Rk1 | 17.14 | 6.18 | 24.02 |
| Rg5 | 29.51 | 0 | 40.98 |
| Rh2 | 5.05 | 0.42 | 20.34 |
| Rh3 | 8.27 | 0.09 | 13.91 |
| PPD | 0.77 | 0.06 | 1.21 |

Examples 23-27

A composition according to the current invention comprises a rare ginsenoside. A composition according to the current invention may also comprise a ginsenoside. Table 7 provides examples of ginsenoside profiles according to the current invention. Table 8 provides examples of rare ginsenoside profiles according to the current invention.

TABLE 7

Examples ginsenoside profile (mg/ml extract).

| example | Rg1 | Re | Rf | Rh1 | Rg2 | Rb1 | Rc | Rb2 | Rd |
|---|---|---|---|---|---|---|---|---|---|
| 23 | 0.01 | 0.01 | 0.01 | 0.01 | 0.4 | 0.4 | 2.2 | 0.01 | 0.8 |
| 24 | 0.1 | 0 | 0 | 0.05 | 0.2 | 0.5 | 0.9 | 0 | 0.5 |
| 25 | 0 | 0 | 0 | 0 | 0.01 | 0.1 | 3 | 0 | 0.01 |
| 26 | 0.2 | 0.05 | 0.1 | 0.05 | 0.2 | 0.5 | 1.8 | 0.01 | 0.6 |
| 27 | 0 | 0.3 | 0 | 0 | 0.01 | 0.1 | 2.5 | 0.1 | 0.5 |

TABLE 8

Example rare ginsenoside profile (mg/ml extract).

| example | Rg6 | Rh4 | Rg3 | PPT | Rk1 | Rg5 | Rh2 | Rh3 | PPD |
|---|---|---|---|---|---|---|---|---|---|
| 23 | 1 | 1.2 | 1.5 | 0.3 | 1.8 | 3.2 | 6.5 | 1.15 | 1.09 |
| 24 | 2 | 2.1 | 2.5 | 0.01 | 1.8 | 1 | 8 | 2 | 0.5 |
| 25 | 0.5 | 0.6 | 0.5 | 0.4 | 2.5 | 4 | 5 | 1.15 | 1 |
| 26 | 1.8 | 2 | 3 | 0.01 | 1.8 | 1 | 4 | 1.1 | 0.5 |
| 27 | 0.7 | 1 | 1 | 0.4 | 1 | 4 | 5 | 2 | 1 |

Table 9 shows the relative results of testing the compositions for cognitive improvement in a patient at five days of intake. A detailed experimental setup for the performance of the compositions is provided in example 31. Examples 23-27 were administered daily enclosed in two capsules as detailed in example 31. Additionally, about 13 mg of ginsan and 3 mg of gintonin were provided in each of said capsules. The performance of the different compositions is force ranked with respect to each other.

TABLE 9

Relative performance examples 23-27.

| example | cognitive improvement |
|---|---|
| 23 | +++ |
| 24 | + |
| 25 | + |
| 26 | ++ |
| 27 | ++ |

Example 28

The current example pertains to a preferred preparation method of a composition according to the current invention. The composition was obtained by growing *ginseng* roots in a hydroponic environment. The hydroponic environment used in the current example is a controlled hydroponic system and is operated as a continuous plug-flow system. The running speed in such plug-flow production plant is increased by a factor of at least three between the seeding stage and harvesting. The effectiveness of the composition was tested in example 31. The composition was obtained by drying, grinding and cooking *ginseng* roots. Tables 10-12 detail the composition.

Analysis Ginsenoside Content

The ginsenoside content and rare ginsenoside content detailed in tables 11-12 was analysed using HPLC. Prior to analysis the grinded *ginseng* roots were subjected to a hydroalcoholic extraction and a subsequent aqueous extraction. The initial hydroalcoholic extraction was performed on 6 kg of the grinded *ginseng* roots.

The hydroalcoholic extraction is effective for the extraction of ginsenosides and gintonin. The hydroalcoholic extraction was performed in two cycles. During a first cycle, a hydroalcoholic extraction was performed under mixing and recirculation for 2 hours 30 min using 35 l of 70% EtOH/30% $H_2O$ at 50° C. The hydroalcoholic solution was recovered by filtration. The second cycle was applied to said filtrate. During said second cycle, another hydroalcoholic extraction was performed under mixing and recirculation for 2 hours 30 min using 30 l of 70% EtOH/30% $H_2O$ at 50° C. The hydroalcoholic solution was again recovered by filtration. Said filtrate was subsequently subjected to an aqueous extraction.

The aqueous extraction is effective for the extraction of the polysaccharide ginsan. The aqueous extraction was performed in two cycles. During a first cycle, an aqueous extraction was performed on said filtrate under mixing for 2 hours 30 min at 80° C. using 30 l of hot water. After said 2-hour 30 min time period, the mixing was stopped and the mixture was heated to 80° C. for another 16 hours. Subsequently, the water fraction and the solid fraction were separated by centrifugation. The solid fraction was subsequently subjected to a second cycle, wherein each step detailed in the first cycle was repeated.

The hydroalcoholic extract was concentrated by evaporation (rotavapor; T°: 50° C.; vacuum: 100-200 mbars). 60 l of hydroalcoholic extract was divided into 4 batches of 15 l. Each batch was concentrated to 5 l and 1.875 l of glycerol was added. The aqueous extract was pre-filtered on 15 μm (by centrifuge filtration) and microfiltered on 0.45 μm. The resulting solution was then ultrafiltered (20 kDa). From about 31 kg of aqueous extract, about 9.3 kg was obtained after ultrafiltration. The concentrated hydroalcoholic extract (57%) was then pooled with the ultrafiltered aqueous extract (43%). Said mixture was analysed by HPLC. The HPLC analysis is detailed in tables 10-12.

Analysis Ginsan Content

The ginsan content detailed in table 11 was analysed by percolating the grinded *ginseng* roots with 5 volumes of 85% ethanol to extract ethanol-soluble materials. The remaining residues were percolated a second time with 5 volumes of distilled water. The water-soluble extracts were concentrated using vacuum evaporator. The concentrate was dialyzed against running tap water for 7 days to completely cut off small molecules with a molecular weight of less than 15 kDa. Four volumes of absolute ethanol were added to precipitate the polysaccharide in the inner dialysate. The precipitate was dried in a vacuum drying oven and was finally used as a red *ginseng* acidic polysaccharide. The extraction and measurements were performed according the study of Choi et al. (Red *Ginseng* Acidic Polysaccharide (RGAP) in Combination with IFN-Y Results in Enhanced Macrophage Function through Activation of the NF-KB Pathway. Hye-Sook CHOI, Kyung-Ho KIM, Eunwha SOHN, Jong-Dae PARK, Byung-Oh KIM, Eun-Yi MOON, Dong-Kwon RHEE, and Suhkneung PYO. Biosci. Biotechnol. Biochem., 72 (7), 1817-1825, 2008).

Analysis Gintonin Content

The gintonin content detailed in table 10 was analysed by extracting *ginseng* using fermented ethanol. Said extract is fractionated with water to obtain a water-soluble and a water-insoluble fraction. The water-insoluble precipitate is the gintonin-enriched fraction (GEF). The extraction and measurements were performed according the study of Choi et al. (A brief method for preparation of gintonin-enriched fraction from *ginseng*. Sun-Hye Choi, Seok-Won Jung, Hyun-Sook Kim, Hyeon-Joong Kim, Byung-Hwan Lee, Joon Yong Kim, Jung-Hyun Kim, Sung Hee Hwang, Hyewon Rhim, Hyoung-Chun Kim, Seung-Yeol Nah. J *Ginseng* Res., 39, 398-405, 2015).

Example 29

The current example pertains to an alternative preparation method of a composition according to the current invention. The composition was obtained by separately extracting rare ginsenosides, ginsan and gintonin from *ginseng*. Example 17 details the constituents of the composition. Ginsan was extracted from *ginseng* by isolating ginsan from an ethanol insoluble fraction of a *ginseng* water extract as is disclosed by Kim et al. (1997). Gintonin was extracted by subsequently partitioning, fractioning and dialyzing a methanol extract obtained from any *ginseng* as is disclosed in EP 2 502 933. Commercially available ginsenosides and rare ginsenosides were bought. The extracts were aliquoted to obtain a simple composition according to the current invention.

Example 30

A 30 wt % rare ginsenoside, 15 wt % ginsan and 3 wt % gintonin composition in a saline solution was evaluated for its effectiveness in improving the cognitive performance of subjects with a learning disability. Performance was evaluated by comparing standardized achievement tests to an intelligence test to determine the potential ability and the actual achievement of each subject. Performance was evaluated prior and after treatment. Treatment comprising a five-day oral administration of 100 mg of the composition. The composition proofed effective in improving cognitive performance in the treated subjects.

Example 31

The current example pertains to an effectiveness study of a *Panax ginseng* herbal preparation. To better exemplify this example reference is made to FIG. 1.

The purpose of this study was to test the effectiveness of a *Panax ginseng* herbal preparation according to the current invention. In particular, the effectiveness in improving cognition in a subject was tested. The study also relates to the effectiveness of the herbal preparation in preventing symptoms related to stress. Such symptoms include fatigue, impaired memory, impaired concentration, impaired attention deficit, restlessness and agitation.

Test Composition

The herbal preparation used in this study was produced according to the methodology exemplified in example 28. Tables 10-12 provide an overview of the average composition of the herbal preparation (n=3). Table 11 provides an overview of the average ginsenoside profile of the herbal preparation (n=3). Table 12 provides an overview of the average rare ginsenoside profile of the herbal preparation (n=3). The profiles only include the tested ginsenosides and rare ginsenosides.

Positive Control

A six years old commercially available *Panax ginseng* Arkopharma was used as positive control. A powdery composition was obtained by cryogenic grinding. Two capsules were provided for daily administration. 382 mg of the powdery composition was aliquoted in said two capsules.

Negative Control

A mixture of cane sugar and rice flour was used as negative control. A powdery composition was enclosed in a capsule. Table 10 provides an overview of the average composition of the negative control (n=3).

TABLE 10

Average tested compositions.

| | rare ginsenoside | ginsan | gintonin | ginsenoside | additional ingredient | formulation |
|---|---|---|---|---|---|---|
| test composition | 31.7 mg | 12.68 mg | 3.17 mg | 5.7 mg | 209 mg rice flour (inactive excipient) and about 135.6 mg other ginseng constituents | two capsules* daily of 209 mg test composition |
| negative control | 0 mg | 0 mg | 0 mg | 0 mg | 418 mg rice flour (inactive excipient) | two capsules* daily containing 209 mg of control |

*Arkopharma caps bought on "NewPharma.be", batch nr. H05178A.

TABLE 11

Average ginsenoside profile test composition.

| ginsenosides | mean (mg/ml extract) |
|---|---|
| Rg1 | 0.00 |
| Re | 0.00 |
| Rf | 0.00 |
| Rh1 | 0.00 |
| Rg2 | 0.37 |
| Rb1 | 0.37 |
| Rc | 2.18 |
| Rb2 | 0.00 |
| Rd | 0.75 |

TABLE 12

| Average rare ginsenoside profile test composition. | |
|---|---|
| Rare ginsenosides | mean (mg/ml extract) |
| Rg6 | 1.00 |
| Rh4 | 1.19 |
| Rg3 | 1.53 |
| PPT | 0.33 |
| Rk1 | 1.74 |
| Rg5 | 3.15 |
| Rh2 | 6.50 |
| Rh3 | 1.15 |
| PPD | 1.09 |

Cognitive Function and Stress Level

The d2 test of attention was used as an estimate for the cognitive performance and stress level in a subject. The d2 Test of Attention is a neuropsychological measure of selective and sustained attention and visual scanning speed. It is a paper and pencil test that asks participants to cross out any letter "d" with two marks around it, above it or below it in an unspecified order. The surrounding distractors are usually similar to the target stimulus, for example a "p" with two marks or a "d" with one or three marks. The original version of the test was created by Brickenkamp (1981) as a cancellation task.

The accuracy of the d2 test is expressed in error rate (%) which is the ratio of errors made to the total number of correct responses for 4 minutes and 40 seconds compared to a determined baseline. To avoid any interference by external factors, measurements were made in the morning at 9 am (baseline) and at the end of workday at 4 μm. The difference between said two periods indicates the potential effect of a substance on the cognitive performance. The error percentage of the d2 test of attention should normally increase between the morning and the afternoon due to stress and fatigue during a workday.

Study

A randomized, double blind, crossover trial was performed on 50 healthy subjects. The subjects were randomized and tested for illegibility. The subjects were prohibited from taking any medicine or dietary supplements. The subjects were prohibited from consuming more than one cup of coffee daily over the duration of the study. An overview of the different time points (t0-t30) is provided below.

t0: A baseline d2 test of attention was performed at 9 am. The cognitive function and stress level of all subjects was measured. The methodology is detailed above.

t1: The d2 test of attention test was repeated at 4 μm.

t2-9: Time points t0 and t1 were repeated for four consecutive days.

t10: Treatment starts. An herbal preparation, a positive control or a negative control (tables 7-9) were administered daily to each subject. Each dose was consumed at 10 am.

t10-15: Time points t0 and t1 were repeated at the first, fifth and twelfth day after start of the treatment.

t16-30: According to crossover design, participants received opposite treatments after a 2-week washout period.

Results

FIG. 1 shows the results of the effectiveness study of example 31. The y-axis of FIG. 1 shows the difference in % error rate (delta (post-pre) workload) of the d2 test between the first and second test during each day. The x-axis indicates the duration of the experiment. A significant reduction in errors were observed on days one, five and twelve for the tested herbal preparation compared to both the positive and negative control. No significant reduction in errors were observed for the positive control compared to the negative control. Moreover, the difference in % error rate is negative for the tested composition on days 1, 5 and 12. A negative difference in error rate indicates an improvement in cognitive performance of the subjects as well as a reduction in stress level during the day.

Example 32

The current example pertains to an effectiveness study of a *Panax ginseng* herbal preparation.

The purpose of this study was to determine whether a *Panax ginseng* herbal preparation according to the current invention is an effective and safe treatment for improving cognitive performance of a subject. The effectiveness of the composition in preventing symptoms of stress, fatigue and impaired cognitive functions was also evaluated.

Test Composition

An herbal test composition was used as disclosed in example 31.

Positive Control

A positive control was used as disclosed in example 31.

Negative Control

A negative control was used as disclosed in example 31.

Cognitive Function and Stress Level

The cognitive performances and stress levels in subjects were estimated by measuring the changes over time in the baseline of electrical activity in the brain of each subject. In particular, a quantitativ-topographic EEG (qEEG) was performed during multiple psychometric tests, followed by a frequency analysis of the data using a Fast Fourier Transformation (FFT). More in particular, responses of electric brain activity were measured by use of spectral power in 17 different brain regions within 6 specially defined frequency ranges (delta, theta, alpha1, alpha2, beta1 and beta2) during a cognitive performance d2-test of attention (d2-test), a memory test (ME-test) and a concentration performance test with financial reward (CPT-test). Additionally, subjects had to fill in a Profile of Mood States (POMS) questionnaire and a stress and coping questionnaire.

Study

A randomized, double blind, crossover trial was performed on 30 subjects between 60 and 75 years old. The subjects were prohibited from taking any medicine or dietary supplements. The subjects were subjected to stringent inclusion and exclusion criteria (e.g. breath alcohol test and qEEG screening).

The selected subjects consumed a daily dose of trial preparation (test composition, positive control or negative control) during three consumption periods (A-B, C-D and E-F). Each consumption periods lasts four weeks. A four-week washout-period was provided between each consumption period. An overview of the different study days (A-F, SC (screening) and FE (final examination)) is provided below.

SC: Procedure steps performed during SC are detailed below. Procedure steps were performed in the order specified below.

Clarification with the subject about the study with subsequent participation of the study.

Breath alcohol test to check for compliance of the subjects.

Safety EEG recording.

Measurement of blood pressure and pulse before qEEG recording.

qEEG-recording-screening: 10 minutes (eyes open (6 min), eyes closed (4 min))—qEEG data comparison to the norm data base.

Determination of suitability.

Appointment for study day A.

A-B: Procedure steps performed on study days of a first consumption period (A-B) are detailed below. Procedure steps were performed in the order specified below.

Breath alcohol test.

Standard breakfast.

Questionnaire—POMS.

Questionnaire—stress and coping.

Blood pressure and pulse measurement before qEEG recording.

qEEG-recording—baseline with mental work. Experimental series used: 6 min qEEG Eyes open, 4 min qEEG Eyes closed, 5 min qEEG and d2-test, 5 min qEEG and ME-test and 5 min qEEG and CPT-test.

Intake of trial preparation.

qEEG-recording after 2 hours—with mental work. Experimental series used: 6 min qEEG Eyes open, 4 min qEEG Eyes closed, 5 min qEEG and d2-test, 5 min qEEG and ME-test and 5 min qEEG and CPT-test.

Questionnaire—POMS.

C-D: Procedure steps detailed for consumption period A-B were repeated for consumption period C-D after a four-week washout period.

E-F: Procedure steps detailed for consumption period A-B were repeated for consumption period E-F after a four-week washout period after consumption period C-D.

FE: Procedure steps performed during FE are detailed below. Procedure steps were performed in the order specified below.

Breath alcohol test.

Standard breakfast.

Blood pressure and pulse measurement.

Safety EEG recording.

Final clinical recording (query).

Discharge from study.

Results

Similarly to example 31, a significant reduction in errors of the d2 test of attention were observed for the test composition at the end of each consumption period compared to both the positive and negative control. No significant reduction in errors were observed for the positive control compared to the negative control. The difference in % error rate is also negative for the test composition at the end of each consumption period. Additionally, more relaxed mental stress conditions were observed for the test composition at the end of each consumption period compared to both the positive and negative control.

Example 33

The current example pertains to an effectiveness study of a *Panax ginseng* herbal preparation.

The purpose of this study was to compare the effects of a *Panax ginseng* herbal preparation according to the current invention (test composition; TC) to a standard white *Ginseng* preparation (positive control; SGP) and a placebo treatment (negative control) on the excitability of pyramidal cells in the hippocampus of rats. Electric induction of hippocampal long-term potentiation (LTP) in vitro was used as a model of time and spatial dependent memory.

Test Composition

A powdered Red *Ginseng* preparation was obtained from hydroponically cultivated Korean *ginseng* (*P. ginseng* Meyer) root. The roots were specially cultivated in controlled conditions to contain 12-15% total ginsenosides and 10-12% rare ginsenosides at Botalys S. A. (Batch No. PGC-190301-001; Ath, Belgium). Harvested roots were air-dried and steamed to red *ginseng*. The red *ginseng* was then powdered and sifted at 300 μm and standardized for the content of rare ginsenosides and the ginsenoside profile. The preparation was standardized for the content of the rare ginsenosides Rh1, Rg2, Rg6, Rh4, Rg3, PPT, Rk1, C(K), Rh2, Rh3, and PPD (calculated as ginsenoside Rb1) and for the total ginsenosides Rg1, Re, Rf, Rh1, Rg2, Rb1, Rc, Rb2, Rd, Rg6, Rh4, Rg3, PPT, Rk1, C(K), Rh2, Rh3, and PPD. The final preparation used in this example was further prepared as to comprise about 6.2 wt % rare ginsenosides, about 7.6 wt % total ginsenosides (rare ginsenosides and classical ginsenosides), about 2.5 wt % ginsan and about 0.60 wt % gintonin.

Positive Control

The SGP is obtained from a *P. ginseng* Meyer powdered root (Batch No. 38837487; Arkopharma Laboratories, Carros, France). The reference standard was analysed and certified by Botalys S. A.

Negative Control

The negative control consisted of a placebo treatment using a 1 wt % glucose mixture in water.

In Vitro Assay on Hippocampal Slices

Hippocampal slice preparation is a validated model for direct analysis of the interaction of substances with living neuronal tissues, through theta burst stimulation. Due to the preservation of the three-dimensional structure of the hippocampal tissue, substance effects on the excitability of pyramidal cells can be studied in a unique manner. The stimulation of Schaffer Collaterals leads to release of glutamate, resulting in excitation of the postsynaptic pyramidal cells. The result of electrical stimulation was recorded as a so-called population spike (pop-spike), FIG. 2. The amplitude of the resulting population spike represents the number of recruited pyramidal cells. The advantages of the model are the possibility of recording in vitro for 8 hours, and also the ability to modify the excitability of the system, in order to create pathophysiological conditions. Analysis of hippocampal pyramidal cell activity by examining changes in amplitude of the population spike, in response to therapeutic interventions, is useful for assessment of their potential efficacy to investigate brain function under strictly controlled laboratory conditions. In the present study, we used this model under ex vivo conditions. *Ginseng* preparations, test composition or SGP, were administered daily for a week and the hippocampus was removed the following day for in vitro characterization of the sensitivity of the intra-hippocampal pathway to electric stimulation. When the repetitive administration succeeded in changing the communication structure within the hippocampus, either higher or lower population spike amplitudes were recorded.

Hippocampal slices were obtained from 22 adult male CD rats at the age of 2 months (Charles River Wiga, Sulzbach, Germany). Rats were kept under a reversed day/night cycle for 2 weeks prior to the start of the experiments to allow recording of in vitro activity from slices during the active phase of their circadian rhythm. Animals were exsanguinated under ether anaesthesia; the total brain was removed and the hippocampal formation was isolated under a micro stereoscopic vision system. The midsection of the hippocampus was fixed to the table of a vibrating microtome (Rhema Labortechnik, Hofheim, Germany) using a cyanoacrylate adhesive, submerged in chilled bicarbonate-buffered saline (artificial cerebrospinal fluid [ACSF]: NaCl:124 mM, KCl: 5 mM, $CaCl_2$): 2 mM, MgSO4: 2 mM, $NaHCO_3$: 26 mM, glucose: 10 mM), and cut into 400 μm thick slices. All slices were pre-incubated for at least 1 h in Carbogen saturated ACSF (pH 7.4) in a pre-chamber before use.

During the experiment, the slices were held and treated in a special super-fusion chamber (List Electronics, Darmstadt, Germany) at 35° C. The preparation was super-fused with ACSF at 180-230 mL/h. Electric stimulation (200 μA constant current pulses of 200 μs pulse width) of the Schaffer Collaterals within the CA2 area and recording of extracellular field potentials from the pyramidal cell layer of CA1 was performed according to conventional electrophysiological methods, using the Labteam Computer system NeuroTool software package (MediSyst GmbH, Linden, Germany). Measurements were performed at 10 min intervals to avoid potentiation mechanisms. The results of four stimulations, each 20 s apart, were averaged for each time point. After obtaining three stable responses to SS, LTP was induced by applying a theta burst stimulus (TBS). The mean amplitudes of three signals were averaged to give mean absolute voltage values (Microvolt)±standard error (SE) of the mean for four slices for one of the experimental conditions. Four or five slices from one rat were used per day.

Slices were used one day after the daily oral administration of the test composition, SGP or glucose 1%, for one week by use of an intra-gastric gavage. Ten slices from 2 animals were averaged to give one final value for each dosage. test composition *Panax ginseng* was administered daily at a dosage of 10 mg/kg, 25 mg/kg, and 50 mg/kg. Arkopharma *Panax ginseng* was administered daily at a dose of 10 mg/kg, 25 mg/kg, and 50 mg/kg.

Statistical Analysis

The results are reported as mean±SD (standard deviation) or ±SE for the indicated number of experiments. All statistical tests were two-sided tests and p-values <0.05 were regarded as significant. The Wilcoxon and Mann Whitney U tests were also used throughout all experimental analyses for comparison of results obtained by vehicle administration and timing with respect to electrophysiological data. Two-way ANOVA was used to examine interaction effects and dose dependent responses between the treatments.

Results

The study aimed to compare effectiveness of the test composition to the effectiveness of SGP by analysis of dose-response relationships. Both preparations were repeatedly administered to rats in three doses for one week. The hippocampal slices were prepared on the day following the last day of treatment, and the excitability of the pyramidal cells was tested in vitro by stimulation of the Schaffer collaterals by means of single electric stimuli, as well as theta burst stimulation leading to long-term potentiation.

Figure 2:
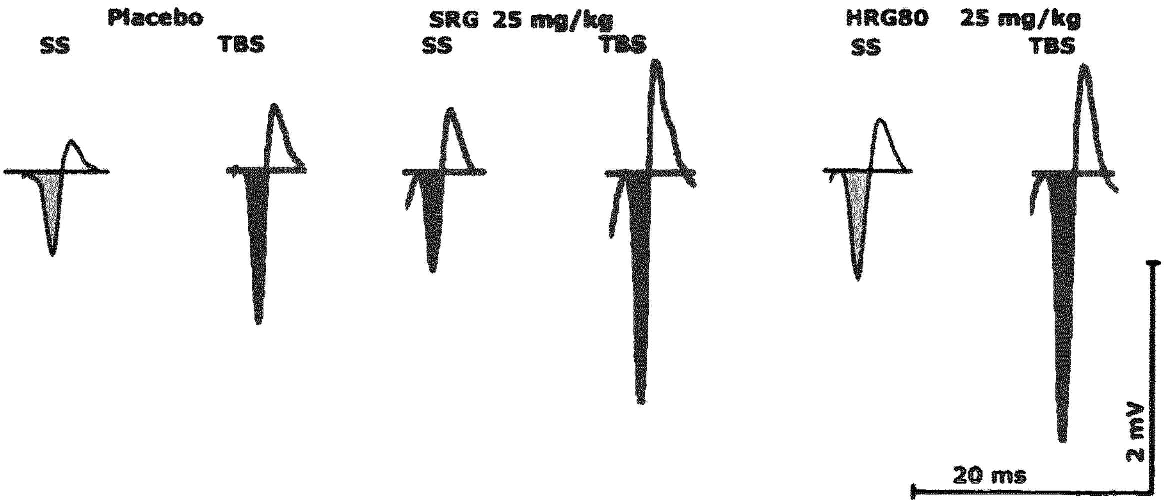
FIG. 2 shows the result of electrical stimulation was recorded as a so-called population spike (pop-spike), wherein the amplitude of the resulting population spike represents the number of recruited pyramidal cells.

Examples for responses (amplitudes of population spikes) to single stimuli (SS) or theta burst stimulation (TBS) are shown for a single slice from a rat under the placebo condition (glucose 1%, 1 ml/kg a day for 1 week), a test composition treated animal (25 mg/kg a day for 1 week) and an SGP treated animal (25 mg/kg a day for one week) in FIG. 2. The test composition treated animals clearly showed higher amplitudes (given in mV) in the presence of single stimuli (SS), as well as after theta burst stimulation (TBS).

Figure 3:
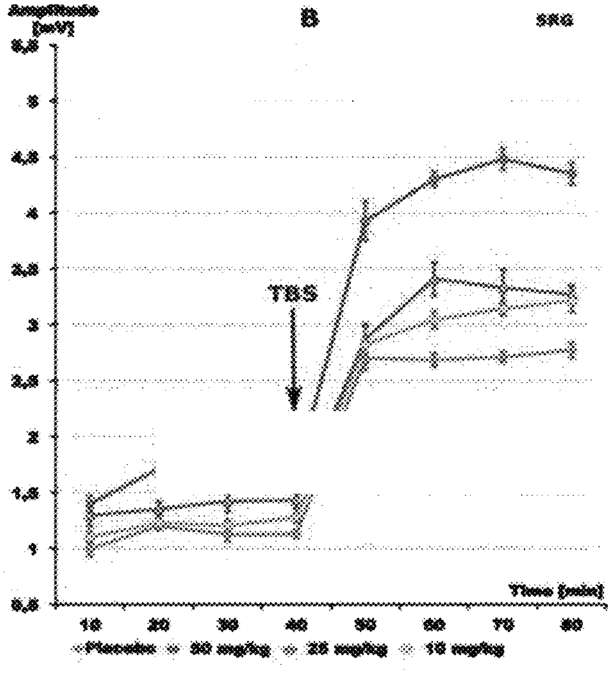
FIG. 3 shows the intra-gastric administration of placebo which resulted in an average amplitude of 1151 pV in the presence of single electric stimuli.

The intra-gastric administration of placebo resulted in an average amplitude of 1151 μV in the presence of single electric stimuli (FIG. 3). Theta burst stimulation (TBS) led to an average amplitude of 2723 μV.

Both preparations enhanced the responses to single and theta burst stimulation. However, higher doses of SGP were needed to achieve effects compatible to the effects of test composition (FIG. 3). Repeated administration of test composition at the doses of 10 mg/kg, 25 mg/kg, and 50 mg/kg for 1 week led to statistically significant increases in the population spike amplitude in comparison to the placebo during single shock stimulation (SS) as well as during TBS. Peak values of 1996 μV after single stimuli and 4787 μV after TBS were measured after administration of 50 mg/kg (FIG. 3A). Repeated administration of SGP at the dose of 10 mg/kg did not show increases in the amplitude of the population spike in comparison to controls after SS (FIG. 3B). Only higher doses of 25 mg/kg or 50 mg/kg SGP significantly increased the population spike amplitude in comparison to the placebo during single shock stimulation (SS), as well as during TBS, reaching amplitudes of 1693 μV and 4377 μV, respectively (p<0.01), FIG. 3B.

Figure 4A:
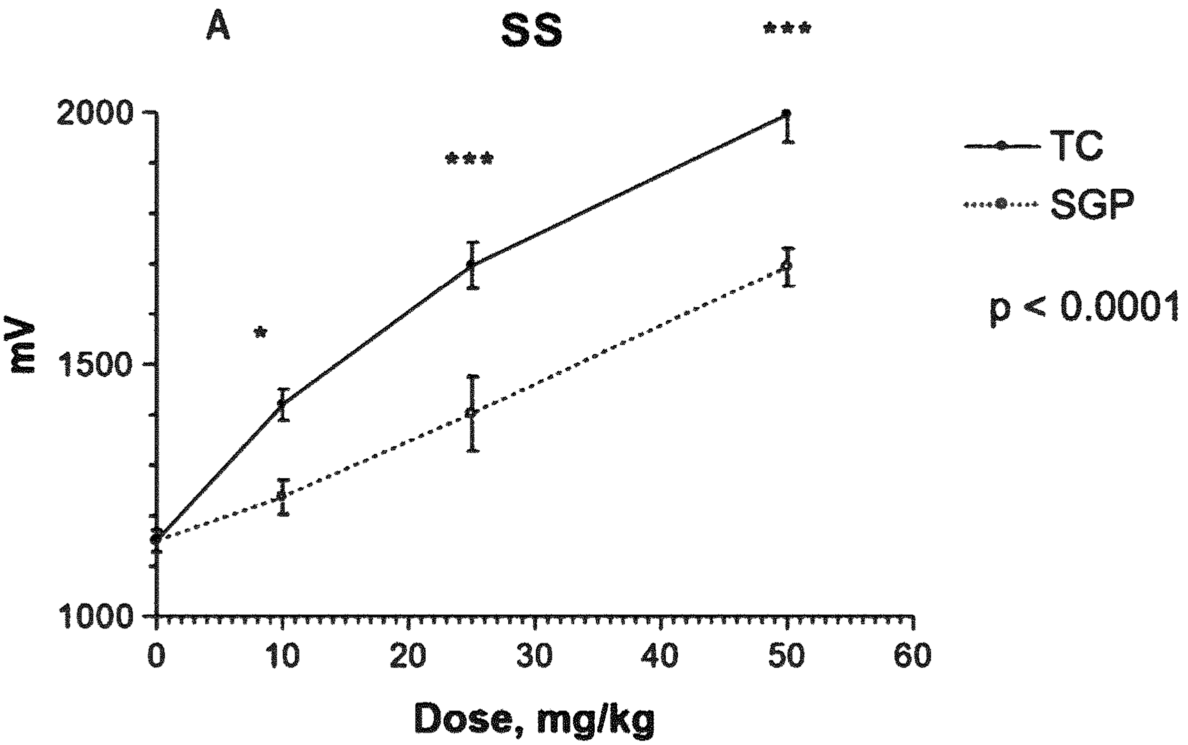
FIGS. 4A and 4B show a direct comparison of the dose-response curves of test composition and SGP reveals a clear quantitative difference in the increase in amplitude of the population spikes in the presence of SS (FIG. 4A, $p<0.0001$), as well as in the presence of TBS, (FIG. 4B, $p=0.0001$).
Figure 4B:
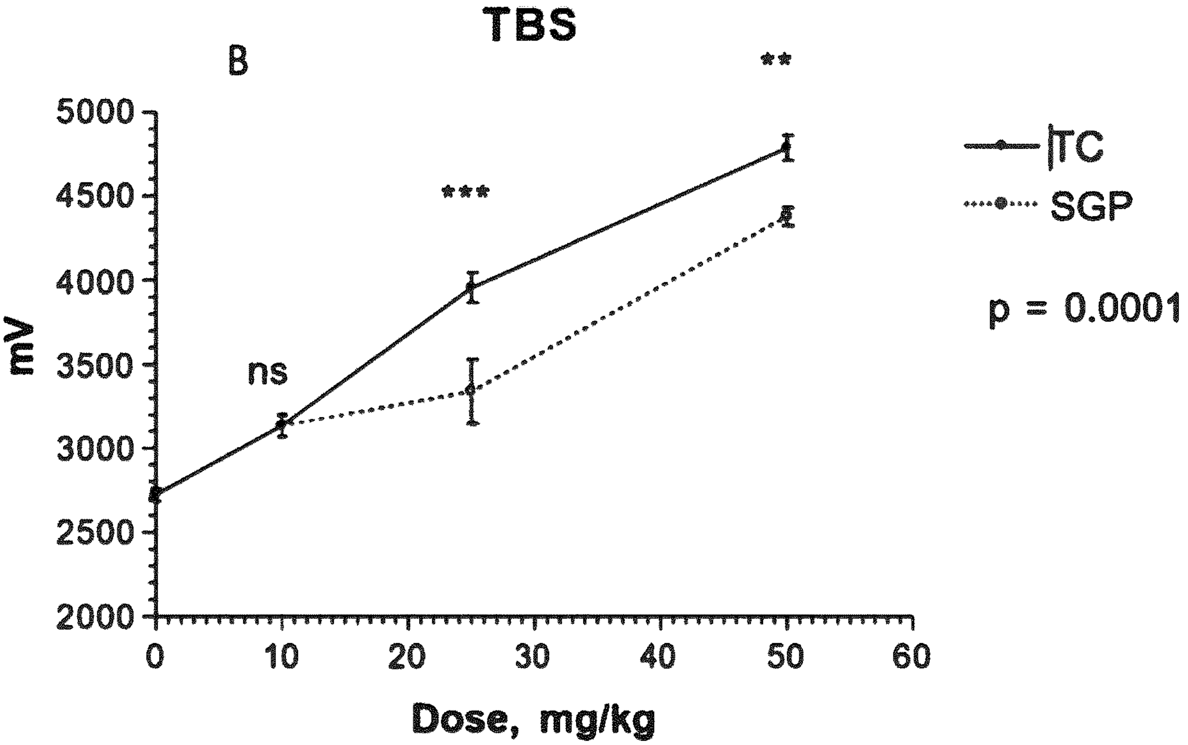

Direct comparison of the dose-response curves of test composition and SGP reveals a clear quantitative difference in the increase in amplitude of the population spikes in the presence of SS (FIG. 4A, p<0.0001), as well as in the presence of TBS, (FIG. 4B, p=0.0001). The effect of test composition on the amplitude of the population spike is significantly stronger than the effect of SGP at the lowest dose of 10 mg/kg (FIG. 4A).

Discussion of Figure

FIG. 2. Documentation of an original signal (from one slice) showing the effects of using single stimuli (SS) or theta burst stimulation (TBS) in the presence of artificial cerebro-spinal fluid (ASCF), glucose 1%-1 ml/kg, test composition 25 mg/kg, SGP 25 mg/kg (for 1 week) in slices from 2 month old rats. The amplitude is calculated from baseline to the down reflection of the signal (shaded). Scales: Time is given in milliseconds (ms), amplitude in millivolts (mV).

FIG. 3. Effects of: A—test composition (10, 25 and 50 mg/kg), B—SGP (10, 25 and 50 mg/kg), and Placebo (glucose 1% 1 ml/kg) on pyramidal cell activity in terms of changes in population spike amplitudes (as voltage on the ordinate). Results as obtained after single stimuli (mean of 10-40 min) or after theta burst stimuli (mean of 50-80 min). Data are given as mean±S.E.M. of n=10 slices from 2 animals/group. SS=single stimuli, TBS=theta burst stimuli.

FIG. 4. Effects of test composition and SGP supplementation for 1 week on hippocampal pyramidal cell population spike amplitudes (μV, mean±SEM) after A—single stimuli (SS, from 20-40 min), and B—theta burst stimuli (TBS, from 60-80 min) ex vivo. Statistically significant interaction effects between dose and response (mV) of two treatments (p=0.0004) were observed in SS (p<0.0001, two-way ANOVA) and TBS (p=0.0001, two-way ANOVA), indicating that the test composition treatment was more beneficial than the *ginseng* control treatment SGP. *—p<0.05, —p<0.01, *—p<0.001, ns—not significant in Bonferroni post-tests.

Example 34

A 30 wt % rare ginsenoside, 15 wt % ginsan and 3 wt % gintonin composition in a saline solution was evaluated for its effectiveness in improving stress levels in athlete subjects diagnosed with a burnout. Performance was evaluated using a Recovery-Stress Questionnaire (Kellmann & Kallus, 2001), Athlete Burnout Questionnaire (Raedeke & Smith, 2001) and Stellenbosch Mood Scale (Terry et al., 2003). Performance was evaluated prior and after treatment. Treatment comprising a five-day oral administration of 100 mg of the composition. The composition proofed effective in reducing stress levels in the treated subjects.

Examples 35-76

A simple composition according to the current invention comprises a rare ginsenoside, a ginsan and a gintonin. The composition can be a composition for oral administration. Table 13 provides an overview of simple compositions for oral administration according to the invention. Table 14 provides an overview of compositions for oral administration also comprising ginsenosides. As a matter of example, other *ginseng* constituents were purged from the samples discussed by examples 35 to 41.

TABLE 13

Simple compositions oral administration.

| example | rare ginsenoside | ginsan | gintonin |
|---|---|---|---|
| 35 | 32 mg | 13 mg | 3 mg |
| 36 | 35 mg | 11 mg | 4 mg |
| 37 | 29 mg | 15 mg | 2 mg |
| 38 | 70 mg | 5 mg | 5 mg |
| 39 | 30 mg | 10 mg | 7 mg |
| 40 | 90 mg | 1 mg | 0.5 mg |
| 41 | 10 mg | 25 mg | 9 mg |

TABLE 14

Compositions oral administration comprising ginsenosides.

| example | rare ginsenoside | ginsan | gintonin | ginsenoside |
|---|---|---|---|---|
| 42 | 1 mg | 30 mg | 10 mg | 15 mg |
| 43 | 100 mg | 0.3 mg | 0.1 mg | 0.5 mg |
| 44 | 20 mg | 25 mg | 9 mg | 0.4 mg |
| 45 | 80 mg | 1 mg | 0.5 mg | 60 mg |
| 46 | 32 mg | 13 mg | 3 mg | 6 mg |
| 47 | 37 mg | 11 mg | 2 mg | 4 mg |
| 48 | 37 mg | 15 mg | 4 mg | 5 mg |

The composition can be a composition for topical administration. A composition for topical administration comprises a *ginseng* agent. A *ginseng* agent comprises a rare ginsenoside, a ginsan, a gintonin and optionally a ginsenoside and/or other ginsenoside constituent. A simple *ginseng* agent comprises a rare ginsenoside, a ginsan and a gintonin. Table 15 provides an overview of simple *ginseng* agents for topical administration according to the invention. Table 16 provides an overview of *ginseng* agents for topical administration also comprising ginsenosides. Examples 49-55 detailed below are expressed by weight of *ginseng* agent. As a matter of example, other *ginseng* constituents were purged from the samples discussed by examples 49 to 55.

TABLE 15

Simple compositions topical administration* (wt. %).

| Example | rare ginsenoside | ginsan | gintonin |
|---|---|---|---|
| 49 | 66 | 27 | 7 |
| 50 | 65 | 30 | 5 |
| 51 | 67 | 27 | 6 |
| 52 | 50 | 35 | 15 |
| 53 | 61 | 37 | 2 |
| 54 | 40 | 59 | 1 |
| 55 | 35 | 45 | 20 |

*Compositions for topical administration were prepared by providing 5 wt. % of ginseng agent (by weight of the composition) in glycerol.

TABLE 16

Compositions topical administration* comprising ginsenosides (wt. %).

| example | rare ginsenoside | ginsan | gintonin | ginsenoside |
|---|---|---|---|---|
| 56 | 65 | 16.6 | 4 | 14.4 |
| 57 | 45 | 19 | 3 | 33 |
| 58 | 55 | 11 | 1.5 | 32.5 |
| 59 | 57 | 24 | 6.5 | 12.5 |
| 60 | 30 | 35 | 10 | 25 |
| 61 | 45 | 30 | 10 | 15 |
| 62 | 20 | 30 | 30 | 20 |

*Compositions for topical administration were prepared by providing 5 wt. % of ginseng agent (by weight of the composition) in glycerol.

Table 17 provides an overview of compositions for oral administration also comprising an additional ingredient, an additive, a carrier and/or an excipient. Throughout the examples, these constituents will be addressed as additional ingredients unless otherwise specified.

TABLE 17

Compositions for oral administration comprising additional ingredient.

| ex. | rare ginsenoside | ginsan | gintonin | ginsenoside | unidentified ginseng constituents | additional ingredient | formulation |
|---|---|---|---|---|---|---|---|
| 63 | 32 mg | 13 mg | 3 mg | 5 mg | 390 mg | 57 mg brown sugar | 2 capsules comprising 250 mg for daily intake. |
| 64 | 40 mg | 15 mg | 5 mg | 10 mg | 510 mg | 200 ml saline | Powdered composition of 580 mg for daily intake. Preferably dissolved in 200 ml saline. |

TABLE 17-continued

Compositions for oral administration comprising additional ingredient.

| ex. | rare ginsenoside | ginsan | gintonin | ginsenoside | unidentified ginseng constituents | additional ingredient | formulation |
|---|---|---|---|---|---|---|---|
| 65 | 31 mg | 12 mg | 4 mg | 6 mg | 315 mg | 632 mg alginic acid | 1 g capsule for daily intake. Preferably after dinner. |
| 66 | 1 mg | 30 mg | 10 mg | 9 mg | 310 mg | 640 mg Arabic gum | 5 tablets of 200 mg for daily intake. |
| 67 | 99 mg | 0.4 mg | 0.1 mg | 0.5 mg | 400 mg | 100 mg rice flour | 2 capsules comprising 300 mg for daily intake. |
| 68 | 20 mg | 25 mg | 9 mg | 15 mg | 580 mg | 350 mg dextrose dissolved in 30 cl water | Powdered composition for daily intake. Preferably dissolved in a dextrose solution. |
| 69 | 80 mg | 4.5 mg | 0.5 mg | 65 mg | 170 mg | >1 g agar | Agar based dessert for daily intake. Preferably after dinner. |

Table 18 provides an overview of compositions for topical administration also comprising an additional ingredient. *Ginseng* agents and other composition constituents are expressed by weight of the composition. *Ginseng* agents in examples 70-76 comprise the following *ginseng* constituents by weight of *ginseng* agent: 67 wt. % rare ginsenoside, 27 wt. % ginsan and 6 wt. % gintonin.

TABLE 18

Compositions for topical administration comprising additional ingredient (wt. %).

| example | ginseng agent | carrier | foaming agent | suitable excipient | other | formulation |
|---|---|---|---|---|---|---|
| 70 | 7% | 20% water | 2% lecithin | 66% | 5% Tween 20 | applied to the skin surface at 0.3 mg/cm$^2$ for 0.5 to 6 h |
| 71 | 0.5% | 10% water | 1% cetrimide | 84.5% | 1% perfume and 3% Tween 20 | applied to the skin surface at 4 mg/cm$^2$ for 1 d |
| 72 | 1% | 35% water | 1% SDS | 62% | 1% vit C | applied to the skin surface at 2 mg/cm$^2$ for at least 30 min |
| 73 | 2% | 15% saline solution | 1% CTAB | 80% | 2% vit C | applied to the skin surface at 1 mg/cm$^2$ daily preferably in the morning |
| 74 | 5% | 25% mineral oil | 5% cetrimide | 64% | perfume 1% | applied to the skin surface at 0.4 mg/cm$^2$ at the evening |

TABLE 18-continued

Compositions for topical administration comprising additional ingredient (wt. %).

| example | ginseng agent | carrier | foaming agent | suitable excipient | other | formulation |
|---|---|---|---|---|---|---|
| 75 | 0.1% | 40% glycerol | 1.5% BAC | 53.4% | 5% vit C | applied to the skin surface at 15 mg/cm$^2$ for 10 min to 6 h |
| 76 | 10% | 10% sesame oil and 5% mineral oil | 1% CPC | 83% | 1% vit C | applied to the skin surface at 0.17 mg/cm$^2$ at noon |

Example 77

A composition according to the current invention comprises a rare ginsenoside. A composition according to the current invention may also comprise a ginsenoside. Table 19 provides an overview of the average ginsenoside profile of a *ginseng* agent of a composition for topical administration according to the invention. Table 20 provides an overview of the average rare ginsenoside profile of a *ginseng* agent of a composition for topical administration according to the invention. A duplicate sample (n=2) was collected from examples 50-63 and 71-77. All additional ingredients were purged from the samples. 42 samples were prepared and analysed in line with the methodology described in example 49.

TABLE 19

Average ginsenoside profile.

| ginsenosides | mean (mg/g dry matter) | min (mg/g dry matter) | max (mg/g dry matter) |
|---|---|---|---|
| Rg1 | 0.02 | 0 | 0.63 |
| Re | 0.2 | 0 | 2.34 |
| Rf | 0.06 | 0 | 0.58 |
| Rh1 | 0.02 | 0 | 0.51 |
| Rg2 | 1.79 | 0 | 3.11 |
| Rb1 | 2.54 | 0 | 7.77 |
| Rc | 1.11 | 0 | 5.09 |
| Rb2 | 1.02 | 0 | 3.99 |
| Rd | 4.38 | 0 | 10.81 |

TABLE 20

Average rare ginsenoside profile.

| rare ginsenosides | mean (mg/g dry matter) | min (mg/g dry matter) | max (mg/g dry matter) |
|---|---|---|---|
| Rg6 | 12.23 | 0 | 16.92 |
| Rh4 | 17.93 | 10.07 | 41.55 |
| Rg3 | 14.17 | 2.6 | 24.18 |
| PPT | 0.58 | 0 | 17.74 |
| Rk1 | 17.14 | 6.18 | 24.02 |
| Rg5 | 29.51 | 0 | 40.98 |
| Rh2 | 5.05 | 0.42 | 20.34 |
| Rh3 | 8.27 | 0.09 | 13.91 |
| PPD | 0.77 | 0.06 | 1.21 |

Examples 78-82

A composition according to the current invention comprises a rare ginsenoside. A composition according to the current invention may also comprise a ginsenoside. Table 21 provides examples of ginsenoside profiles in a composition for topical administration. Table 22 provides examples of rare ginsenoside profiles in a composition for topical administration. Samples were prepared and analysed in line with the methodology described in example 49.

TABLE 21

Examples ginsenoside profile (mg/ml extract).

| example | Rg1 | Re | Rf | Rh1 | Rg2 | Rb1 | Rc | Rb2 | Rd |
|---|---|---|---|---|---|---|---|---|---|
| 78 | 0.01 | 0.01 | 0.01 | 0.01 | 0.4 | 0.4 | 2.2 | 0.01 | 0.8 |
| 79 | 0.1 | 0 | 0 | 0.05 | 0.2 | 0.5 | 0.9 | 0 | 0.5 |
| 80 | 0 | 0 | 0 | 0 | 0.01 | 0.1 | 3 | 0 | 0.01 |
| 81 | 0.2 | 0.05 | 0.1 | 0.05 | 0.2 | 0.5 | 1.8 | 0.01 | 0.6 |
| 82 | 0 | 0.3 | 0 | 0 | 0.01 | 0.1 | 2.5 | 0.1 | 0.5 |

TABLE 22

Example rare ginsenoside profile (mg/ml extract).

| example | Rg6 | Rh4 | Rg3 | PPT | Rk1 | Rg5 | Rh2 | Rh3 | PPD |
|---|---|---|---|---|---|---|---|---|---|
| 78 | 1 | 1.2 | 1.5 | 0.3 | 1.8 | 3.2 | 6.5 | 1.15 | 1.09 |
| 79 | 2 | 2.1 | 2.5 | 0.01 | 1.8 | 1 | 8 | 2 | 0.5 |
| 80 | 0.5 | 0.6 | 0.5 | 0.4 | 2.5 | 4 | 5 | 1.15 | 1 |
| 81 | 1.8 | 2 | 3 | 0.01 | 1.8 | 1 | 4 | 1.1 | 0.5 |
| 82 | 0.7 | 1 | 1 | 0.4 | 1 | 4 | 5 | 2 | 1 |

Example 83

The current example pertains to a preferred preparation method of a composition according to the current invention. The composition was obtained by growing *ginseng* roots in a hydroponic environment. The hydroponic environment used in the current example is a controlled hydroponic system and is operated as a continuous plug-flow system. The running speed in the plug-flow production plant is increased by a factor of at least three between the seeding stage and harvesting. The composition was obtained by drying and subsequently grinding and cooking *ginseng* roots. The grinded *ginseng* roots were subjected to different extraction steps to obtain the different composition constituents.

Hydroalcoholic Extraction

The initial hydroalcoholic extraction, according to this example, was performed on 6 kg of the grinded *ginseng* roots. The hydroalcoholic extraction is effective for the extraction of rare ginsenosides, ginsenosides and gintonin. The hydroalcoholic extraction was performed in two cycles.

During a first cycle, a hydroalcoholic extraction was performed under mixing and recirculation for 2 hours 30 min using 35 l of 70% EtOH/30% $H_2O$ at 50° C. The hydroalcoholic extract was recovered by filtration. The second cycle was applied to said filtrate. During said second cycle, another hydroalcoholic extraction was performed under mixing and recirculation for 2 hours 30 min using 30 l of 70%, EtOH/30% $H_2O$ at 50° C. The hydroalcoholic extract was again recovered by filtration. Both hydroalcoholic extracts can be pooled. The resulting hydroalcoholic extract* is rich in rare ginsenosides, ginsenosides and gintonin. The filtrate is rich in ginsan.

Said hydroalcoholic extract was fractionated with water to obtain a water-soluble fraction, a water insoluble fraction and a water-insoluble precipitate fraction. The water-insoluble precipitate fraction is the gintonin-enriched fraction. The water insoluble fraction is rich in rare ginsenosides and ginsenosides.

Aqueous Extraction

The filtrate obtained after the hydroalcoholic extraction was subjected to an aqueous extraction. The aqueous extraction is effective for the extraction of the polysaccharide ginsan. The aqueous extraction was performed in two cycles.

During a first cycle, an aqueous extraction was performed on said filtrate under mixing for 2 hours 30 min at 80° C. using 30 l of hot water. After said 2-hour 30 min time period, the mixing was stopped and the mixture was heated to 80° C. for another 16 hours. Subsequently, the aqueous extract and the solid fraction were separated by centrifugation. The solid fraction was subsequently subjected to a second cycle, wherein each step detailed in the first cycle was repeated to obtain the final aqueous extract**.

Said aqueous extract was concentrated using a vacuum evaporator. The concentrate was dialyzed against running tap water for 7 days to completely cut off small molecules with a molecular weight of less than 15 kDa. Four volumes of absolute ethanol were added to precipitate the polysaccharide in the inner dialysate. The precipitate was dried in a vacuum drying oven and was finally used as a *ginseng* acidic polysaccharide.

Composition

The composition constituents (i.e. the hydroalcoholic solution, the gintonin-enriched fraction and the *ginseng* acidic polysaccharide) were aliquoted to obtain a composition according to the invention at the desired ratios.

Analysis

The rare ginsenoside, ginsenoside, ginsan and gintonin content were analysed. The hydroalcoholic extract prior to fractionation was pooled with the aqueous extract to obtain a composition according to the invention. Said mixture was analysed by HPLC. The composition comprised about 7,072 mg/ml extract ginsan and about 1,768 mg/ml extract gintonin. The ginsenoside and rare ginsenoside content is detailed in tables 23 and 24.

TABLE 23

Average ginsenoside profile.

| ginsenosides | mean (mg/ml extract) |
|---|---|
| Rg1 | 0.00 |
| Re | 0.00 |
| Rf | 0.00 |
| Rh1 | 0.00 |
| Rg2 | 0.37 |
| Rb1 | 0.37 |
| Rc | 2.18 |
| Rb2 | 0.00 |
| Rd | 0.75 |

TABLE 24

Average rare ginsenoside profile.

| Rare ginsenosides | mean (mg/ml extract) |
|---|---|
| Rg6 | 1.00 |
| Rh4 | 1.19 |
| Rg3 | 1.53 |
| PPT | 0.33 |
| Rk1 | 1.74 |
| Rg5 | 3.15 |
| Rh2 | 6.50 |
| Rh3 | 1.15 |
| PPD | 1.09 |

Example 84

The current example pertains to a preferred preparation method of an extract. The prepared extract can be used in commercial applications. Such applications include oral administrable compositions and topical formulations. Prior to preparing said extract, the hydroalcoholic solution* and the aqueous extract**, as disclosed hereabove in example 83, are treated.

Treatment Hydroalcoholic Extract*

The hydroalcoholic extract*, as disclosed hereabove in example 83, can be concentrated. The following illustrates a preferred method.

The hydroalcoholic solution*, which is rich in rare ginsenosides, ginsenosides and gintonin, is initially concentrated under a partial vacuum (e.g. Rotavapor Büchi R 220; 100 to 200 mbar; bath temperature 50° C.; 90 RPM; condenser temperature 5° C.). Glycerol is added to the concentrate as humectant.

In a pilot setup, 60 L of hydroalcoholic solution* was divided in 4 batches of 15 L. Each of said 4 batches were concentrated to a volume of about 5 L. 1,875 L of food grade glycerol was added to each of said 4 concentrated batches. The net yield obtained by said pilot setup, starting from 5.97 kg of *ginseng* roots is about 27.5 L of glycerol concentrate[1].

Treatment Aqueous Extract**

The aqueous extract**, as disclosed hereabove in example 83, can be concentrated. The following illustrates a preferred method.

The aqueous extract**, which is rich in ginsan, is treated in three different filtration steps. In a first step, the extract is filtered in two cycles using a filtration centrifuge with a mesh size of about 15 μm (e.g. filtration centrifuge by Rousselet Robatel). In a second step, the extract is microfiltered with a mesh size of about 0.45 μm. In a third step, the extract is ultrafiltered in three cycles with a mesh size of 20 kDa.

In a pilot setup, 74.4 kg of aqueous extract** was filtered using a filtration centrifuge with a mesh size of about 15 μm resulting in about 30 L of extract. Said 30 L extract (corresponding with 31.6 kg of *ginseng* root) was microfiltered over a surface of 0,064 $m^2$ at a debit of 28 L/h. After 11 hours of filtration, about 30 kg of extract was recovered. Said 30 kg of recovered extract was ultrafiltered with a mesh size of about 20 kDa over a surface of about 0.02 $m^2$ at a debit of about 1.4 to about 1.6 L/h and at a pressure of about 1.3 to 1.8 bar. After three days, 9.3 kg of extract[2] was recovered.

Extract Preparation

The following illustrates a preferred procedure for preparing an extract.

The extract[2] is preserved in a freezer. Prior to handling, the extract[2] must be thawed. 69 g of the extract[2] is pipetted and aliquoted in a 250 mL autoclavable bottle. 81 g of the glycerol concentrate[1] is pipetted and aliquoted in said 250 mL autoclavable bottle. The solution in the bottle is homogenized by mixing. said bottle is provided in an evacuated autoclavable bag with a control bottle comprising 250 mL of distilled water and eight dropper bottles. After autoclavation, the solution is aliquoted to the dropper bottles under sterile conditions in a laminar flow hood. Such solution can also be addressed as totum extract. Such solution preferably comprises at least 1 wt. % and at most 30 wt. % of rare ginsenoside, ginsan and gintonin, ideally about 12 wt. %.

Example 85

The current example pertains to an alternative preparation method of a composition according to the current invention. The composition was obtained by separately extracting rare ginsenosides, ginsan and gintonin from *ginseng*. Example 49 details the constituents of the composition. Ginsan was extracted from *ginseng* by isolating ginsan from an ethanol insoluble fraction of a *ginseng* water extract as is disclosed by Kim et al. (1997). Gintonin was extracted by subsequently partitioning, fractioning and dialyzing a methanol extract obtained from any *ginseng* as is disclosed in EP 2 502 933. Optionally, the methanol extract is filtered using an ultrafiltration with a mesh size of about 20 kDa. Commercially available ginsenosides and rare ginsenosides were bought. The extracts were aliquoted to obtain a simple composition according to the current invention.

Example 86

A 7.5 wt. % rare ginsenoside, 3.75 wt. % ginsan and 0.75 wt. % gintonin *ginseng* composition by weight of *ginseng* agent was evaluated for its effectiveness in improving skin conditions in subjects. 400 mg of the composition in combination with 100 mg brown sugar was administered orally in a capsule. Evaluated skin conditions are skin moisturisation, skin whitening, wrinkle reduction and other aging associated symptoms. An extract of a store-bought red *ginseng* was used as positive control.

Skin moisturization was evaluated in subjects with dry skin. Skin moisturization was evaluated using a Nova™ DPM 9003 Dermal Phase Meter, which measures impedance-based capacitance readings by using varying frequencies of the applied alternating current. The Nova™ DPM 9003 measures the relative water content of the stratum corneum. Skin whitening was evaluated in subjects with scar-induced hyperpigmentation. Skin whitening was evaluated by the subjects themselves and by a skilled technician. Wrinkle reduction and anti-aging were evaluated in subjects between 40 and 55 years. Wrinkle reduction and anti-aging were evaluated by the subjects themselves and by a skilled technician.

Performance of the composition and the positive control were evaluated in view of the tested skin conditions prior and after a five-day treatment. Treatment comprising a five-day oral administration of 100 mg of the composition or positive control. The composition proofed effective in increasing moisture content in the treated subjects. The composition also proofed effective in visually decreasing scar-induced hyperpigmentation as well as visually decreasing signs of skin aging such as wrinkles. The composition also proofed more effective in view of the positive control.

Example 87

A totum extract comprising 7.5 wt. % rare ginsenoside, 3.75 wt. % ginsan and 0.75 wt. % gintonin by weight of extract was evaluated for its effectiveness in improving skin conditions in subjects. The extract was provided at 2.0 wt. % by weight of the composition and was administrated topically (cream or serum). Evaluated skin conditions are skin moisturisation, skin whitening, wrinkle reduction and other aging associated symptoms. An extract of a store-bought red *ginseng* was used as positive control.

Skin conditions were evaluated according to the methodologies describes in example 85.

Performance of the composition and the positive control were evaluated in view of the tested skin conditions prior and after a five-day treatment. Treatment comprising a five-day topical administration of about 1 mg/$cm^2$ of the composition or the positive control. The composition was applied to three different regions of the face of a subject (i.e. forehead, eye area and the corners of the mouth). The composition proofed effective in increasing moisture content in the treated subjects. The composition also proofed effective in visually decreasing scar-induced hyperpigmentation as well as visually decreasing signs of skin aging such as wrinkles. The composition also proofed more effective in view of the positive control.

Example 88

A totum extract comprising 10 wt. % rare ginsenoside, 5 wt. % ginsan and 1 wt. % gintonin by weight of extract was evaluated for its effectiveness in improving skin conditions. The extract was evaluated on in vitro cell cultures. Evaluated skin conditions are skin whitening, wrinkle reduction and other aging associated symptoms. An extract of a store-bought red *ginseng* was used as positive control.

Skin whitening was evaluated in vitro by evaluation of melanogenesis, in particular by measurement of the expression of protein involved into the skin pigmentation. Wrinkle reduction and anti-aging were evaluated in in-vitro models. Wrinkle reduction and anti-aging were evaluated by the measurements of the expression of protein involved into the skin matrix degradation (MMP) and regeneration (collagen).

Performance of the composition and the positive control were evaluated in view of the tested conditions prior and after treatment. The composition proofed effective in decreasing the skin pigmentation as well as decreasing signs of skin aging such as wrinkles. The composition also proofed more effective in view of the positive control.

The invention claimed is:

1. A method of manufacturing a composition, said composition comprising a rare ginsenoside, a ginsan and a gintonin, and said manufacturing method comprising:

extracting rare ginsenoside, ginsan, and gintonin from a *ginseng*, the extraction comprising the steps of:

growing the *ginseng* in a hydroponic environment;

harvesting a root from said grown *ginseng;* drying and/or grinding said harvested root;

cooking said harvested *ginseng* root;

mixing and recirculating the cooked *ginseng* root in a hydroalcoholic solution to yield an extracted solution; and filtering the extracted solution to yield the composition, wherein a weight ratio in the composition of ginsan to gintonin is from 1:100 to 500:1 and wherein a weight ratio of rare ginsenosides to ginsan and gintonin is from 1:40 to 250:1.

2. The composition prepared by the method according to claim 1, wherein a weight ratio of rare ginsenoside to ginsan is from 1:30 to 300:1 within the composition.

3. The composition prepared by the method according to claim 1, wherein a weight ratio of rare ginsenoside to gintonin is from 1:10 to 1000:1 within the composition.

4. The composition prepared by the method according to claim 1, wherein said rare ginsenoside is selected from the group consisting of Rg6, Rh4, Rg3, PPT, Rkl, Rg5, Rh2, Rh3 and PPD.

5. The composition prepared by the method according to claim 1, wherein said composition further comprises a ginsenoside extracted from the *ginseng*, whereby said ginsenoside is selected from the group consisting of Rgl, Re, Rf, Rhl, Rg2, Rbl, Rc, Rb2 and Rd.

6. The composition prepared by the method according to claim 1, wherein said rare ginsenoside comprises Rg5 and Rh2 and one or more rare ginsenosides selected from the group consisting of C-K, Rg6, Rh4, Rg3, PPT, Rkl, Rh3 and PPD; and wherein a ratio of a Rg5 and Rh2 to a total amount of rare ginsenoside is from 1:4 to 1:1.

7. The composition prepared by the method according to claim 1, for use in treatment or prevention of an impaired cognition in a subject, whereby said composition is provided in a pharmaceutically and/or cosmetically acceptable carrier and optionally one or more pharmaceutically acceptable excipients.

8. The composition prepared by the method according to claim 1, in a pharmaceutically or cosmetically acceptable carrier and one or more pharmaceutically acceptable excipients, for use as a medicament for treatment or prevention of stress in a subject, or a medicament for treatment or prevention of stress in a subject whereby the cognitive performance of said subject is improved.

9. The composition prepared by the method according to claim 1, wherein said composition is in combination with a pharmaceutically and/or cosmetically acceptable carrier suitable for topical administration, wherein said combination is a cream, a lotion, or a spray.

10. A method for improving cognitive performance in a subject, the method comprising orally and/or topically administering the composition of claim 1 to the subject, the composition comprising a rare ginsenoside, a ginsan and a gintonin, whereby said composition is administered to the subject in a pharmaceutically and/or cosmetically acceptable carrier and optionally one or more pharmaceutically acceptable excipients.

11. The method according to claim 10, further comprising treating impaired cognition in a subject.

12. The method according to claim 10, whereby said composition comprises a daily effective dose of rare ginsenoside of at least 1 mg and at most 100 mg.

13. A method for treating an impaired cognition or a dermatological disease in a subject with a medicament prepared by the extraction method of claim 1, wherein the medicament is provided in a dose formulation comprising:

a daily effective dose of rare ginsenoside of at least 1 mg and at most 100 mg;

a daily effective dose of ginsan of at least 0.3 mg and at most 30 mg; and a daily effective dose of gintonin of at least 0.1 mg and at most 10 mg.

14. The method according to preceding claim 13 for preparation of a composition comprising a rare ginsenoside, a ginsan and a gintonin, wherein a weight ratio of ginsan to gintonin is from 1:100 to 500:1 and wherein a weight ratio of rare ginsenosides to ginsan and gintonin is 1:40 to 250:1 for use in treatment or prevention of an impaired cognition in a subject, whereby said composition is provided in a pharmaceutically and/or cosmetically acceptable carrier and optionally one or more pharmaceutically acceptable excipients.

* * * * *